United States Patent
Wong et al.

(10) Patent No.: US 9,689,039 B2
(45) Date of Patent: Jun. 27, 2017

(54) SALIVARY BIOMARKERS FOR LUNG CANCER DETECTION

(75) Inventors: David T. Wong, Beverly Hills, CA (US); Lei Zhang, Los Angeles, CA (US); Hua Xiao, Irvine, CA (US); Hui Zhou, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/025,130

(22) Filed: Feb. 10, 2011

(65) Prior Publication Data

US 2011/0207622 A1    Aug. 25, 2011

Related U.S. Application Data

(60) Provisional application No. 61/303,205, filed on Feb. 10, 2010.

(51) Int. Cl.
*C12Q 1/68* (2006.01)
*G01N 33/574* (2006.01)

(52) U.S. Cl.
CPC .......... *C12Q 1/6886* (2013.01); *C12Q 1/689* (2013.01); *G01N 33/57423* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2008/0286273 A1 | 11/2008 | Starmans et al. | |
| 2009/0297525 A1* | 12/2009 | Depinho et al. | 424/139.1 |
| 2011/0123441 A1* | 5/2011 | Lippman et al. | 424/1.49 |

FOREIGN PATENT DOCUMENTS

| | | |
|---|---|---|
| JP | 2007531879 | 11/2007 |
| JP | 2008536480 | 9/2008 |
| WO | WO 02/073204 A2 | 9/2002 |
| WO | WO 2004/046386 A1 | 6/2004 |
| WO | 2005/098445 | 10/2005 |
| WO | 2006/105642 | 10/2006 |
| WO | WO 2009/154790 A2 | 12/2009 |

OTHER PUBLICATIONS

Ranzi et al., The Signaling Adapters Fibroblast Growth Factor Receptor Substrate 2 and 3 Are Activated by the Thyroid TRK Oncoproteins; Endocrinology, vol. 144, No. 3, pp. 922-928, 2003.*

Zhang et al., Role of epithelial cell fibroblast growth factor receptor substrate 2 alpha in prostate development, regeneration and tumorigenesis; Development, vol. 135, pp. 775-784, 2008.*

Collins et al., The application of genomic and proteomic technologies in predictive, preventative and personalized medicine; Vascular Pharmacology, vol. 45, pp. 258-267, pp. 2006.*

Subramanian et al., Gene Expression-Based Prognostic Signatures in Lung Cancer: Ready for Clinical Use?; J Natl Cancer Inst, vol. 102, No. 7, pp. 464-474, 2010.*

Li et al., Salivary transcriptome diagnostics for oral cancer detection; Clinical Cancer Research, vol. 10, pp. 8442-8450, 2004.*

Screen captures from NCBI Gene Expression Omnibus Accession No. GPL96, Affymetrix U133A Gene Chip, accessed Aug. 10, 2014.*

Takada et al., "Prediction of Lymph Node Metastasis by Analysis of Gene Expression Profiles in Non-small Cell Lung Cancer," *Journal of Surgical Research*, 2004, 122:61-69.

Sato et al., "The FRS2 family of docking/scaffolding adaptor protein as therapeutic targets of cancer treatment," *Expert Opin. Ther. Targets*, 2009, 13(6):689-700.

Marek et al., "Fibroblast Growth Factor (FGF) and FGF Receptor-Mediated Autocrine Signaling in Non-Small-Cell Lung Cancer Cells," *Mol Pharmacol.*, 2009, 75:196-207.

Ghosh et al., "PDZK1 and GREB1 are Estrogen-regulated Genes Expressed in Hormone-responsive Breast Cancer," *Cancer Research*, 2000, 60:6367-6075.

Tonon et al., "High-resolution genomic profiles of human lung cancer," *PNAS*, 2005, 102(27):9625-9630.

Park, et al., "Characterization of RNA in Saliva," *Clinical Chemistry*, 2006, 52(6):988-994.

Li, et al., "RNA Profiling of Cell-free Saliva Using Microarray Technology," *J Dent Res*, 2004, 83(3):199-203.

Gao, et al., "Systemic Disease-Induced Salivary Biomarker Profiles in Mouse Models of Melanoma and Non-Small Cell Lung Cancer," *PLoS ONE*, 2009, vol. 4, Issue 6, pp. 1-10.

Li, et al., "Salivary Transcriptome Diagnostics for Oral Cancer Detection," *Clinical Cancer Research*, 2004, 10:8442-8450.

Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.

Zimmermann et al., "Genomic Targets in Saliva", Annals of the New York Academy of Sciences, vol. 1098, pp. 184-191 (Mar. 2007).

* cited by examiner

*Primary Examiner* — Addison D Ault
(74) *Attorney, Agent, or Firm* — Riverside Law LLP

(57) ABSTRACT

Presented herein are biomarkers related to lung cancer. The presently identified salivary biomarkers create the basis for a lung cancer detection bioassay with sensitivity and specificity. Means and methods for evaluating the data generated using multiple biomarkers in order to validate findings and further use of the multiplexed lung cancer assay in clinical, diagnostic and therapeutic uses is also included.

4 Claims, 1 Drawing Sheet

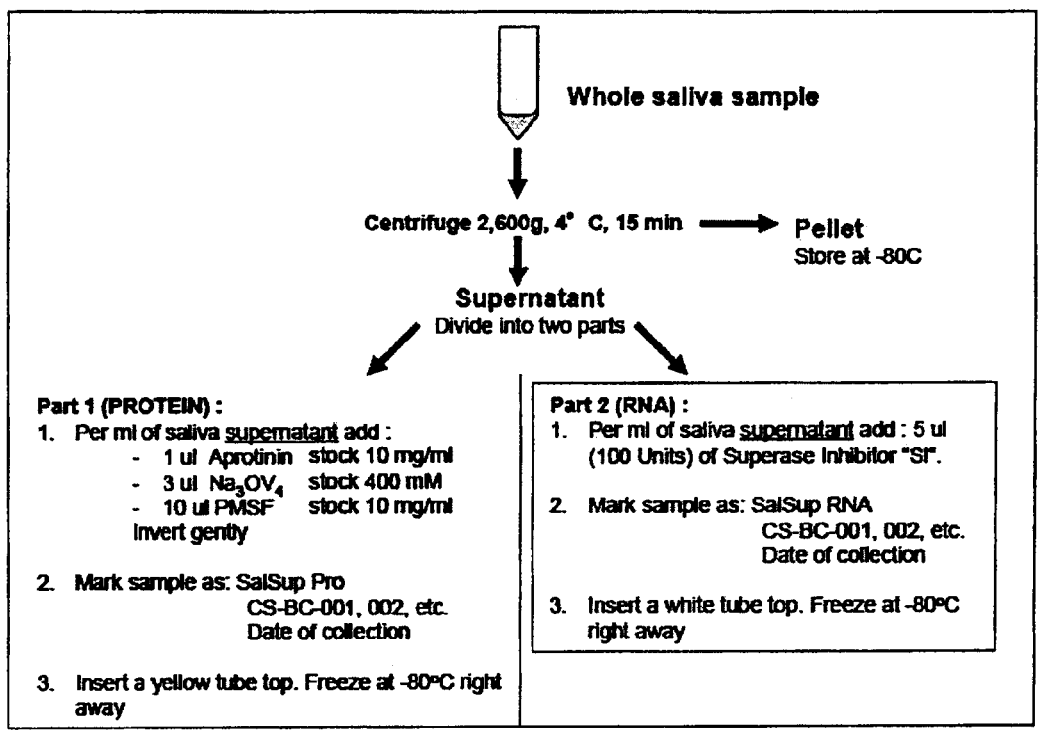

SALIVARY BIOMARKERS FOR LUNG CANCER DETECTION

CROSS-REFERENCES TO RELATED APPLICATIONS

The present application claims priority to provisional application U.S. Ser. No. 61/303,205, filed Feb. 10, 2010, herein incorporated by reference in its entirety.

STATEMENT AS TO RIGHTS TO INVENTIONS MADE UNDER FEDERALLY SPONSORED RESEARCH OR DEVELOPMENT

This invention was made with Government support under Grant No. DE016275, awarded by the National Institutes of Health. The Government has certain rights in this invention.

BACKGROUND

According to the National Cancer Institute, lung cancer is the leading cause of cancer death (hypertext transfer protocol://www.cancer.gov/cancertopics/types/lung). In 2008, approximately 215,000 new lung cancer patients were diagnosed in the United States alone. Roughly 87% of these patients will have on-small cell lung cancer (NSCLC).

Smoking, particularly of cigarettes, is by far the main contributor to lung cancer. In the U.S., it is estimated that there are 45 million current and 45 million former smokers at risk for developing lung carcinoma. Lung cancer is estimated to remain a major health problem for at least the next 50 years.

Over 75% of lung cancer cases are diagnosed in late stages because there remains no practical way to screen the large numbers of people at risk. Early detection offers the promise of improved cure rates.

Attempts have been made to identify and stratify individuals at high risk for developing lung cancer and early detection. Initially spectum cytology and chest X-ray were used as screening tools. Unfortunately these procedures failed to increase the number of curable cases.

These procedures were supplanted by computerized tomography (CT) scans, which are more sensitive than chest X-ray. Unfortunately, broad application of CT screening of the at risk population has several drawbacks including high false positives (detection of benign lung nodules) and poor ability to identify central tumors. Because of the high false positive rate, approaching 50%, it is estimated that for every lung cancer death prevented by CT screening, two unnecessary invasive procedures will be conducted.

As such, a need exists for methods useful for detecting lung cancer, and in particular biomarkers that can detect early stages of the disease and are largely non-invasive.

BRIEF SUMMARY OF THE INVENTION

In accordance with some embodiments of the invention, a method of determining the likelihood of the presence or occurrence of lung cancer in a test subject is provided. The disclosed method includes analyzing a saliva sample from the subject with an assay that specifically detects a biomarker in the saliva sample, the biomarker selected from the group of: CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:9), Zinc Alpha2-Glycoprotein (SEQ ID NO: 10), *Porphyromonas catoniae* 16S rRNA, *Campylobacter showae* 16S rRNA, *Streptococococcus salivaris* 16S rRNA, *Campylobacter rectus* 16S rRNA, *Veillonella parvula* 16S rRNA, *Kigella oralis* 16S rRNA, and *Granulicatella adiacens* 16S rRNA. The relative occurrence of the biomarkers is determined and compared to a control, thereby allowing the lung cancer status of the test subject to be determined.

In some embodiments, a method of determining the likelihood of the presence or occurrence of lung cancer in a test subject is provided, the method entailing the detection of at least two biomarkers in a saliva sample. In other embodiments, a method of determining the likelihood of the presence or occurrence of lung cancer in a test subject is provided, the method entailing the detection of *Porphyromonas catoniae* 16S rRNA and *Camplylobacter showae* 16S rRNA. The relative occurrence of these biomarkers or these biomarkers and others in these instances is determined and compared to a control, for example, thereby allowing the lung cancer status of the test subject to be determined.

In some embodiments, a method of determining the likelihood of the presence or occurrence of lung cancer in a test subject is provided, the method entailing the detection of at least three biomarkers in a saliva sample. In other embodiments, a method of determining the likelihood of the presence or occurrence of lung cancer in a test subject is provided, the method entailing the detection of GREB1, CCNI and FRS. In other embodiments, a method of determining the likelihood of the presence or occurrence of lung cancer in a test subject is provided, the method entailing the detection of. The relative occurrence of these biomarkers or these biomakers and others in these instances is determined and compared to a control, for example, thereby allowing the lung cancer status of the test subject to be determined.

In other embodiments, the method of determining the likelihood of the presence or occurrence of lung cancer in a test subject includes an assay in which a nucleic acid encoding at least one biomarker is detected. The nucleic acid can be detected by, for example, mass spectroscopy, polymerase chain reaction (PCR), microarray hybridization, thermal sequencing, capillary array sequencing, or solid phase sequencing.

In other embodiments, the method of determining the likelihood of the presence or occurrence of lung cancer in a test subject includes an assay in which a polypeptide encoding at least one biomarker is detected. The polypeptide can be detected by, for example, enzyme-linked immunosorbent assay (ELISA), Western blot, flow cytometry, immunofluorescence, immunohistochemistry, or mass spectroscopy.

In accordance with other embodiments of the invention, a method for assessing the efficacy of a therapy is disclosed. This method includes analyzing a first saliva sample from the subject with an assay that specifically detects a biomarker, the biomarker selected from the group consisting of CCNI, EGFR, FGF9, GREB1 protein, LZTS, BRAF, FRS2, ANXA1, Hp2, Zinc Alpha2-Glycoprotein, *Porphyromonas catoniae* 16S rRNA, *Campylobacter showae* 16S rRNA, *Streptococococcus salivaris* 16S rRNA, *Campylobacter rectus* 16S rRNA, *Veillonella parvula* 16S rRNA, *Kigella oxalis* 16S rRNA, and *Granulicatella adiacens* 16S rRNA. This first analysis provides a first expression profile. A therapy is applied to a subject. An analysis of a second saliva sample from the subject is undertaken with an assay that specifically detects at least two biomarkers selected from the group consisting of CCNI, EGFR, FGF9, GREB1 protein, LZTS, BRAF, FRS2, ANXA1, Hp2, Zinc Alpha2-Glycoprotein, *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oxalis* 16S rRNA, and *Granulicatella adiacens* 16S rRNA thereby providing a second expression profile. The first and second expression profiles are compared in order to assess the efficacy of a therapy.

In another embodiment, a solid support is provided, wherein the solid support includes a capture binding probe selective for at least two biomarkers selected from the group of CCNI, EGFR, FGF9, GREB1 protein, LZTS, BRAF, FRS2, *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oralis* 16S rRNA, and *Granulicatella adiacens* 16S rRNA. In some embodiments, a first and a second solid support are provided, wherein the first solid support includes a capture binding probe selective for a biomarker selected from the group consisting of CCNI, EGFR, FGF9, GREB1 protein, LZTS, BRAF, FRS2, *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oralis* 16S rRNA, and *Granulicatella adiacens* 16S rRNA and wherein the second solid support includes a capture binding ligand selective for a biomarker selected from ANXA1, Hp2, Zinc Alpha2-Glycoprotein, and Calprotectin.

In some embodiments, the capture binding ligand of the kit is an antibody. In another embodiment the kit provides one or more primers for the selective amplification of a biomarker, wherein the biomarker is selected from the group of: CCNI, EGFR, FGF9, GREB1 protein, LZTS, BRAF, FRS2, *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oralis* 16S rRNA, and *Granulicatella adiacens* 16S rRNA. In some embodiments one or more of the primers possess a detectable label.

In accordance with some embodiments of the invention, a method of determining the likelihood of the presence or occurrence of lung cancer in a test subject is provided. The disclosed method includes analyzing a saliva sample from the subject with an assay that specifically detects at least seventeen biomarkers in the saliva sample. The biomarkers are selected from the group of: CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:9), Zinc Alpha2-Glycoprotein (SEQ ID NO: 10), *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oxalis* 16S rRNA, and *Granulicatella adiacens* 16S rRNA. The relative occurrence of at least seventeen biomarkers is determined and compared to a control, thereby allowing the lung cancer status of the test subject to be determined.

In any of the embodiments above, wherein a method for determining the likelihood of the presence or occurrence of lung cancer in a test subject, the number of biomarkers used can be 1, 2, 3, 4, 5, 6, 7, 8, 9, 10, 11, 12, 13, 14, 15, 16, 17 or more.

These and other embodiments, features and potential advantages will become apparent with reference to the following description and drawings.

BRIEF DESCRIPTION OF THE DRAWINGS

FIG. 1 is a schematic representation of the protocol for saliva collection.

DETAILED DESCRIPTION OF THE INVENTION

Introduction

Early detection of lung cancer offers the promise of easier treatment (smaller surgeries, less radiation or chemotherapy) and improved survival. Conventional screening (CT, X-ray, sputum cytology) has a less-than desirable sensitivity and specificity. A sensitive assay to identify biomarkers using non-invasively collected specimens is therefore ideal for lung cancer detection.

Biomarkers, whether produced by healthy individuals or by individuals affected by specific systemic disease, can be used as tell-tale molecules for monitoring health status, disease onset, treatment responsiveness, and outcome.

Saliva is a readily accessible source of biomarkers. As a clinical diagnostic biofluid, saliva offers many advantages; sample collection is simple, non-invasive, and causes less anxiety on the part of patients. The use of saliva also offers a cost-effective approach for large-scale screens.

The present invention discloses the diagnostic/prognostic significance of seventeen salivary biomarkers, including detection of the 16S rRNA indicative of seven bacteria strains. These biomarkers include CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:9), Zinc Alpha2-Glycoprotein (SEQ ID NO:10), *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oralis* 16S rRNA, *Granulicatella adiacens* 16S rRNA, and combinations thereof, in lung cancer detection. Detection of these and other biomarkers in saliva are useful for diagnosis and prognosis of lung cancer.

Methods for detecting salivary biomarkers (proteins and nucleic acids) include techniques such as ELISA, PCR, for example, RT-PCR or mass spectroscopy, alone or in combination with other markers. Any specific probe can be used for detection, such as an antibody, a receptor, a ligand, RT-PCR etc. Mass spectroscopy can also be used for protein detection. Thus, the present invention can be used alone or as a complement to traditional antigen analysis to enhance the diagnosis of lung and other cancers.

DEFINITIONS

CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:8), Zinc Alpha2-Glycoprotein (SEQ ID NO:9), *Porphyromonas catoniae* 16S rRNA, *Campylobacter showae* 16S rRNA, *Streptococcus salivaris* 16S rRNA, *Campylobacter rectus* 16S rRNA, *Veillonella parvula* 16S rRNA, *Kigella oralis* 16S rRNA, *Granulicatella adiacens* 16S rRNA refer to nucleic acids, e.g., gene, DNA, pre-mRNA, mRNA, and polypeptides, polymorphic variants, alleles, mutants, and interspecies homologs that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein. The nucleic acids and proteins of the invention include both naturally occurring or recombinant molecules. The nucleic acid or protein sequence is provided, for example, in SEQ ID NOs: 1-9.

*Porphyromonas catoniae*, *Campylobacter showae*, *Streptococcus salivaris*, *Campylobacter rectus*, *Veillonella parvula*, *Kigella oralis*, *Granulicatella adiacens* refer to bacterial strains. These strains and others can be detected in a sample using any number of methods, including, for example, the detection of 16S rRNA (ribonucleic acid or deoxyribonucleic acid), the detection of chromosomal DNA, mRNA or by culturing bacteria from a sample in an appropriate growth medium under appropriate growth conditions.

"Cancer" refers to human cancers and carcinomas, sarcomas, adenocarcinomas, lymphomas, leukemias, etc., including solid and lymphoid cancers, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma.

"Therapeutic treatment" and "cancer therapies" refers to chemotherapy, hormonal therapy, radiotherapy, and immunotherapy.

The terms "overexpress," "overexpression" or "overexpressed" interchangeably refer to a protein that is transcribed or translated at a detectably greater level, usually in a cancer cell, in comparison to a normal cell. The term includes overexpression due to transcription, post transcriptional processing, translation, post-translational processing, cellular localization (e.g, organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "cancer-associated antigen" or "tumor-specific marker" or "tumor marker" interchangeably refers to a molecule (typically protein or nucleic acid such as RNA) that is expressed in the cell, expressed on the surface of a cancer cell or secreted by a cancer cell in comparison to a normal cell, and which is useful for the diagnosis of cancer, for providing a prognosis, and for preferential targeting of a pharmacological agent to the cancer cell. Oftentimes, a cancer-associated antigen is overexpressed in a cancer cell in comparison to a normal cell, for instance, about 1.2-fold over expression, about 2-fold overexpression, about 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

It will be understood by the skilled artisan that markers may be used singly or in combination with other markers for any of the uses, e.g., diagnosis or prognosis of lung cancer, disclosed herein.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site hypertext transfer protocol:// www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1987-2005, Wiley Interscience)).

An example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (hypertext transfer protocol://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single or double-stranded form, and complements thereof.

Specifically refers to ability of a ligand to bind to a target with an affinity at least 1.2, 1.5, 2, 3, 5, 8, 10, 20, 50, 100, 150, 200, 500, 1000, or more fold greater than a ligand not specific for the target.

Unless otherwise indicated, a particular nucleic acid sequence also implicitly encompasses conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include fluorescent dyes, electron-dense reagents, enzymes (for example, as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" means a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')2, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

Biomarkers

Biomarkers may originate from epidemiological studies, animal studies, pathophysiological considerations and end-organ experiments. Ideally, a biomarker will have a high predictive value for a meaningful outcome measure, can be or is validated in appropriately designed prospective trials, reflects therapeutic success by corresponding changes in the surrogate marker results, and should be easy to assess in clinical practice.

Biomarkers can be used in conjunction with other diagnostic tools or used alone.

The term "surrogate marker," "biomolecular marker," "biomarker" or "marker" (also sometimes referred to herein as a "target analyte," "target species" or "target sequence") refers to a molecule whose measurement provides information as to the state of a subject. In various exemplary embodiments, the biomarker is used to assess a pathological state. Measurements of the biomarker may be used alone or combined with other data obtained regarding a subject in order to determine the state of the subject. In one embodiment, the biomarker is "differentially present" in a sample taken from a subject of one phenotypic status (e.g., having a disease) as compared with another phenotypic status (e.g., not having the disease). In one embodiment, the biomarker is "differentially present" in a sample taken from a subject undergoing no therapy or one type of therapy as compared with another type of therapy. Alternatively, the biomarker may be "differentially present" even if there is no phenotypic difference, e.g. the biomarkers may allow the detection of asymptomatic risk.

A biomarker may be over-expressed (over-abundant) or under-expressed (under abundant) relative to a control. The biomarker can be an allelic variant, truncated or mutated form of a wild-type nucelic acid or protein. The biomarker can be a splice variant.

A biomarker may be determined to be "differentially present" in a variety of ways, for example, between different phenotypic statuses if the mean or median level (particularly the expression level of the associated mRNAs as described below) of the biomarker in the different groups is calculated to be statistically significant. Common tests for statistical significance include, among others, t-test, ANOVA, Kruskal-Wallis, Wilcoxon, Mann-Whitney and odds ratio.

As described herein, a biomarker may be, for example, a small molecule, an analyte or target analyte, a nucleic acid, a protein, a metabolite or any derivative thereof or any and all combinations of these molecules, with proteins and nucleic acids finding particular use in the invention. As will be appreciated by those in the art, a large number of analytes may be detected using the present methods; basically, any biomarker for which a binding ligand, described below, may be made may be detected using the methods of the invention.

In various embodiments, the biomarkers used in the panels of the invention can be detected either as proteins or as nucleic acids (e.g. mRNA or cDNA transcripts) in any combination. In various embodiments, the protein form of a biomarker is measured. As will be appreciated by those in the art, protein assays may be done using standard techniques such as ELISA assays. In various embodiments, the nucleic acid form of a biomarker (e.g., the corresponding mRNA) is measured. In various exemplary embodiments, one or more biomarkers from a particular panel are measured using a protein assay and one or more biomarkers from the same panel are measured using a nucleic acid assay.

As will be appreciated by those in the art, there are a large number of possible proteinaceous target analytes and target species that may be detected using the present invention. The term "protein," "polypeptide" or "oligopeptide" refers to at least two or more peptides or amino acids joined by one or more peptide bonds. A protein or an amino acid may be naturally or nonnaturally occurring and may be also be an analog, a derivative or a peptidomimetic structure. The term "protein" refers to wild-type sequences, variants of wild-type sequences and either of these containing analogs or derivatized amino acids. In various embodiments, variants of the sequences described herein, including proteins and nucleic acids based on e.g. splice variants, variants comprising a deletion, addition, substitution, fragments, preproprotein, processed preproprotein (e.g. without a signaling peptide), processed proprotein (e.g. resulting in an active form), nonhuman sequences and variant nonhuman sequences may be used as biomarkers.

In various embodiments, the biomarker is a nucleic acid. The term "nucleic acid" or "oligonucleotide" or grammatical equivalents herein means at least two nucleotides covalently linked together. A nucleic acid of the present invention will generally contain phosphodiester bonds, although in some cases, as outlined below, for example in the use of binding ligand probes, nucleic acid analogs are included that may have alternate backbones.

Biomarkers can also be bacterial nucleic acids or proteins. The oral cavity is a large reservoir of bacteria, with more than 700 species or phylotypes, of which over 50% have not been cultivated. In some embodiments, assessing bacterial flora composition and dynamic changes are biomarkers for lung cancer.

A recently developed 16S rRNA-based oligonucleotide microarray (Human Oral Microbe Identification Microarray) made it possible to profile the oral bacterial flora in patients with and without lung cancer. In some embodiments, the presence, absence, or level of 16S rRNA from bacteria in a sample may correlate with a disease or condition. "Bacteria" refers to small prokaryotic organisms (linear dimensions of around 1 µm) with non-compartmentalized circular DNA and ribosomes of about 70 S. "16S RNA" refers to a nucleic acid component of the 30S subunit of prokaryotic ribosomes; the gene that encodes the 16S rRNA or the 16S rRNA itself. Bacterial strains of species or phylotypes have less than about a 2% difference in 16S rRNA. Closely related species or phylotypes generally have between about a 2% and about a 4% difference in 16S rRNA, whereas a genus often has between about a 5% and about a 10% difference in 16S rRNA.

To resolve the identity of bacterial populations, probes on a microarray can be designed, for example, to take advantage of conserved features of the 16S rRNA gene. For example, probes complementary to the more conserved features regions identify species in a large phylogenetic group, each group corresponding to a higher taxon (for example, domain, phylum, class, order, or family). Probes complementary to more variable regions distinguish genera and species.

Biomarkers can also include micro RNAs. "MicroRNAs" (miRs) refers to a class of small naturally occurring non-coding RNAs (18-24 nucleotides) that regulate gene expression. Many microRNAs are well conserved across species and they are present in a broad range of species: plants, nematodes, fruit flies and humans. MicroRNAs have partially or perfect complementary sequence to one or more messenger RNA molecules (mRNAs) and their main function is to negatively regulate the expression of genes. In particular, microRNAs bind to the 3' untranslated regions of mRNAs (3-UTR) thus leading to down regulation of mRNAs in a variety of ways such as mRNA cleavage, translational repression and deadenylation.

A variety of experimental approaches and different techniques have been used to identify new microRNAs, as well as to study their expression pattern in the different biological processes. The cloning and identification of new microRNAs have been successfully done from size fractioned RNA samples using small RNA cloning approaches. Other approaches is as putative microRNAs homologues to microRNAs that already have been described in other species or using computational approaches alone or in combination with microarray analysis and sequence-directed cloning.

One of the first techniques used for detection and profiling of microRNAs was Northern Blotting, where hybridization is done with a complementary 32P, digoxigenin-labeled oligo or modified Locked-nucleic-acid (LNA) oligonucleotides after gel separation.

Other techniques that have been developed to specifically detect microRNAs are a modified invader assay (a synthetic oligonucleotide, the probe, which is in an appropriate overlap-flap structure is enzymatically cleavage by a structure-specific 5* nuclease) and in situ hybridization (using fluorescent-labeled complementary probes containing chemically modified nucleotides e.g. LNAs). Another widely used technique for detection and profiling of microRNAs is the use of oligonucleotide micro-array based detection platforms either with DNA capture probes or using modified Locked-nucleic-acid (LNA) oligonucleotides in which the ribose moiety is modified with an extra bridge that connects the 2'-0 and 4'-C atoms.

In addition, quantitative real-time PCR (reverse transcriptase/polymerase chain reaction using Taqman or SYBR green technology) has been used for detection and profiling of precursor or mature microRNAs. This technique is sensitive and requires low amounts of starting material for the detection of individual mature microRNAs. Taqman microRNA arrays have been developed that provide the sensitivity of the qRT-PCR, while at the same time enables the simultaneously detection of different microRNAs in one sample.

Biomarkers can also include metabolites. "Metabolite" or "small molecule" refers to organic and inorganic molecules which are present in a sample. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000).

The metabolites of the cell are generally found free in solution. A "metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

A metabolic profile can be developed by analyzing a sample using for example, techniques such as GC-MS (gas chromatography-mass spectrometry) and LC-MS (liquid chromatography-mass spectrometry).

Biomarker Panels

Any combination of the biomarkers described herein is used to assemble a biomarker panel, which is detected or measured as described herein. As is generally understood in the art, a combination may refer to an entire set or any subset or subcombination thereof. The term "biomarker panel," "biomarker profile," or "biomarker fingerprint" refers to a set of biomarkers. As used herein, these terms can also refer to any form of the biomarker that is measured. Thus, if CCNI is part of a biomarker panel, then either CCNI mRNA, for example, or protein, for example, could be considered to be part of the panel. While individual biomarkers are useful as diagnostics, combination of biomarkers can sometimes provide greater value in determining a particular status than single biomarkers alone. Specifically, the detection of a plurality of biomarkers in a sample can increase the sensitivity and/or specificity of the test. Thus, in various embodiments, a biomarker panel may include 1, 2, 3, 4, 5, 6, 7, 8, 9, 10, 11, 12, 13, 14, 15, 16, 17, or more types of biomarkers. In various exemplary embodiments, the biomarker panel consists of a minimum number of biomarkers to generate a maximum amount of information. Thus, in various embodiments, the biomarker panel consists of 1, 2, 3, 4, 5, 6, 7, 8, 9, 10, 11, 12, 13, 14, 15, 16, 17, or more types of biomarkers. Where a biomarker panel "consists of" a set of biomarkers, no biomarkers other than those of the set are present. In exemplary embodiments, the biomarker panel consists of 1 biomarkers disclosed herein. In various embodiments, the biomarker panel consists of 2 biomarkers disclosed herein. In various embodiments, the biomarker panel consists of 3 biomarkers disclosed herein. In various embodiments, the biomarker panel consists of 4 or more biomarkers disclosed herein.

In various exemplary embodiments, the biomarker panel comprises or consists of a biomarker selected from the group of CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:8), Chain B, Crystal Structure of the Complex formed between MHc-Like Zinc Alpha2-Glycoprotein and Pro1, *Porphyromonas catoniae* 16S rRNA, *Campylobacter showae* 16S rRNA, *Streptocococcus salivaris* 16S rRNA, *Campylobacter rectus* 16S rRNA, *Veillonella parvula* 16S rRNA, *Kigella oralis* 16S rRNA.

A biomarker can also be a clinical parameter. The term "clinical parameter" refers to all non-sample or non-analyte biomarkers of subject health status or other characteristics, such as, without limitation, age, ethnicity, gender, family history, height, and weight.

The biomarkers of the invention show a statistically significant difference in lung cancer diagnosis. In various embodiments, diagnostic tests that use these biomarkers alone or in combination show a sensitivity and specificity of at least about 85%, at least about 90%, at least about 95%, at least about 98% and about 100%.

Measurement and Detection of Biomarkers

Biomarkers generally can be measured and detected through a variety of assays, methods and detection systems known to one of skill in the art. The term "measuring," "detecting," or "taking a measurement" refers to a quantitative or qualitative determination of a property of an entity, for example, quantifying the amount or concentration of a molecule or the activity level of a molecule. The term "concentration" or "level" can refer to an absolute or relative quantity. Measuring a molecule may also include determining the absence or presence of the molecule. Various methods include but are not limited to refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

In one embodiment in the present invention are biochip assays. By "biochip" or "chip" herein is meant a composition generally comprising a solid support or substrate to which a capture binding ligand (also called an adsorbent, affinity reagent or binding ligand, or when nucleic acid is measured, a capture probe) is attached and can bind either proteins, nucleic acids or both. Generally, where a biochip is used for measurements of protein and nucleic acid biomarkers, the protein biomarkers are measured on a chip separate from that used to measure the nucleic acid biomarkers. For nonlimiting examples of additional platforms and methods useful for measuring nucleic acids, see Publications US/2006/0275782, US/2005/0064469 and DE10201463. In various embodiments, biomarkers are measured on the same platform, such as on one chip. In various embodiments, biomarkers are measured using different platforms and/or different experimental runs.

By "binding ligand," "capture binding ligand," "capture binding species," "capture probe" or grammatical equivalents herein is meant a compound that is used to detect the presence of or to quantify, relatively or absolutely, a target analyte, target species or target sequence (all used interchangeably) and that will bind to the target analyte, target species or target sequence. Generally, the capture binding ligand or capture probe allows the attachment of a target species or target sequence to a solid support for the purposes of detection as further described herein. Attachment of the target species to the capture binding ligand may be direct or indirect. In exemplary embodiments, the target species is a biomarker. As will be appreciated by those in the art, the composition of the binding ligand will depend on the composition of the biomarker. Binding ligands for a wide variety of biomarkers are known or can be readily found using known techniques. For example, when the biomarker is a protein, the binding ligands include proteins (particularly including antibodies or fragments thereof ($F_{ab}$s, etc.) as discussed further below) or small molecules. The binding ligand may also have cross-reactivity with proteins of other species. Antigen-antibody pairs, receptor-ligands, and carbohydrates and their binding partners are also suitable analyte-binding ligand pairs. In various embodiments, the binding ligand may be nucleic acid. Nucleic acid binding ligands find particular use when proteins are the targets; alternatively, as is generally described in U.S. Pat. Nos. 5,270,163; 5,475,096; 5,567,588; 5,595,877; 5,637,459; 5,683,867; 5,705,337 and related patents, hereby incorporated by reference, nucleic acid "aptamers" can be developed for binding to virtually any biomarker. Nucleic acid binding ligands also find particular use when nucleic acids are binding targets. There is a wide body of literature relating to the development of binding partners based on combinatorial chemistry methods. In these embodiments, when the binding ligand is a nucleic acid, preferred compositions and techniques are outlined in PCT Publication WO/1998/020162, hereby incorporated by reference.

In various exemplary embodiments, the capture binding ligand is an antibody. These embodiments are particularly useful for the detection of the protein form of a biomarker.

Detecting or measuring the level (e.g. the transcription level) of a biomarker involves binding of the biomarker to a capture binding ligand, generally referred to herein as a "capture probe" when the mRNA of the biomarker is to be detected on a solid support. In that sense, the biomarker is a target sequence. The term "target sequence" or "target nucleic acid" or grammatical equivalents herein means a nucleic acid sequence that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. In some embodiments, measuring a nucleic acid can thus refer to measuring the complement of the nucleic acid. It may be any length, with the understanding that longer sequences are more specific.

The target sequence may also comprise different target domains; for example, a first target domain of the sample target sequence may hybridize to a first capture probe, a second target domain may hybridize to a label probe (e.g. a "sandwich assay" format), etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the target sequence, the first target domain may be located either 5' to the second domain, or 3' to the second domain.

When nucleic acids are used as the target analyte, the assays of the invention can take on a number of embodiments. In one embodiment, the assays are done in solution format, using any number of solution based formats. In one embodiment, end-point or real time PCR formats are used, as are well known in the art. These assays can be done either as a panel, in individual tubes or wells, or as multiplex assays, using sets of primers and different labels within a single tube or well. In addition to PCR-based solution formats, other formats can be utilized, including, but not limited to for example ligation based assays utilizing FRET dye pairs. In this embodiment, only upon ligation of two (or more) probes hybridized to the target sequence is a signal generated.

In many embodiments, the assays are done on a solid support, utilizing a capture probe associated with the surface. As discussed herein, the capture probes (or capture binding ligands, as they are sometimes referred to) can be covalently attached to the surface, for example using capture probes terminally modified with functional groups, for example amino groups, that are attached to modified surfaces such as silanized glass. Alternatively, non-covalent attachment, such as electrostatic, hydrophobic/hydrophilic adhesion can be utilized. As is appreciated by those in the art and discussed herein, a large number of attachments are possible on a wide variety of surfaces.

In this embodiment, the assays can take on a number of formats. In one embodiment, the target sequence comprises a detectable label, as described herein. In this embodiment, the label is generally added to the target sequence during amplification of the target in one of two ways: either labeled primers are utilized during the amplification step or labeled dNTPs are used, both of which are well known in the art. The label can either be a primary or secondary label as discussed herein. For example, in one embodiment, the label on the primer and/or a dNTP is a primary label such as a fluorophore. Alternatively, the label may be a secondary label such as biotin or an enzyme; for example, in one embodiment, the primers or dNTPs are labeled with biotin, and then a streptavidin/label complex is added. In one embodiment, the streptavidin/label complex contains a label such as a fluorophore. In an alternative embodiment, the streptavidin/label complex comprises an enzymatic label. For example, the complex can comprise horseradish peroxidase, and upon addition of TMB, the action of the horseradish peroxidase causes the TMB to precipitate, causing an optically detectable event. This has a particular benefit in that the optics for detection does not require the use of a fluorimeter.

In alternate embodiments, the solid phase assay relies on the use of a labeled soluble capture ligand, sometimes referred to as a "label probe" or "signaling probe" when the target analyte is a nucleic acid. In this format, the assay is a "sandwich" type assay, where the capture probe binds to a first domain of the target sequence and the label probe binds to a second domain. In this embodiment, the label probe can also be either a primary (e.g. a fluorophore) or a secondary (biotin or enzyme) label. In one embodiment, the label probe comprises biotin, and a streptavidin/enzyme complex is used, as discussed herein. As above, for example, the complex can comprise horseradish peroxidase, and upon addition of TMB, the action of the horseradish peroxidase causes the TMB to precipitate, causing an optically detectable event.

Detection of a target species in some embodiments requires a "label" or "detectable marker" (as described below) that can be incorporated in a variety of ways. Thus, in various embodiments, the composition comprises a "label" or a "detectable marker." In one embodiment, the target species (or target analyte or target sequence) is labeled; binding of the target species thus provides the label at the surface of the solid support.

In embodiments finding particular use herein, a sandwich format is utilized, in which target species are unlabeled. In these embodiments, a "capture" or "anchor" binding ligand is attached to the detection surface as described herein, and a soluble binding ligand (frequently referred to herein as a "signaling probe," "label probe" or "soluble capture ligand") binds independently to the target species and either directly or indirectly comprises at least one label or detectable marker.

By "label" or "labeled" herein is meant that a compound has at least one molecule, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) enzymes; although labels include particles such as magnetic particles as well. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes and others described in the 6th Edition of the Molecular Probes Handbook by Richard P. Haugland, hereby expressly incorporated by reference. Additional labels include nanocrystals or Q-dots as described in U.S. Pat. No. 6,544,732 incorporated by reference.

In various embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc. Secondary labels can also include additional labels.

In various embodiments, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof ($F_{ab}$s, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In the sandwich formats of the invention, an enzyme serves as the secondary label, bound to the soluble capture ligand. Of particular use in some embodiments is the use of horseradish peroxidase, which when combined with 3,3',5, 5'-tetramethylbenzidine (TMB) forms a colored precipitate which is then detected. In some cases, the soluble capture ligand comprises biotin, which is then bound to a enzyme-streptavidin complex and forms a colored precipitate with the addition of TMB.

In various embodiments, the label or detectable marker is a conjugated enzyme (for example, horseradish peroxidase). In various embodiments, the system relies on detecting the precipitation of a reaction product or on a change in, for example, electronic properties for detection. In various embodiments, none of the compounds comprises a label.

As used herein, the term "fluorescent signal generating moiety" or "fluorophore" refers to a molecule or part of a molecule that absorbs energy at one wavelength and re-emits energy at another wavelength. Fluorescent properties that can be measured include fluorescence intensity, fluorescence lifetime, emission spectrum characteristics, energy transfer, and the like.

Signals from single molecules can be generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, *Scanning Electron Microscopy: Physics of Image Formation and Microanalysis,* 2nd Edition (Springer, 1998); Nie et al, *Anal. Chem.,* 78: 1528-1534 (2006); Hecht et al, *Journal Chemical Physics,* 112: 7761-7774 (2000); Zhu et al, editors, *Near-Field Optics: Principles and Applications* (World Scientific Publishing, Singapore, 1999); Drmanac, PCT Publication WO/2004/076683; Lehr et al, *Anal. Chem.,* 75: 2414-2420 (2003); Neuschafer et al, *Biosensors & Bioelectronics,* 18: 489-497 (2003); Neuschafer et al, U.S. Pat. No. 6,289,144; and the like.

Thus, a detection system for fluorophores includes any device that can be used to measure fluorescent properties as discussed above. In various embodiments, the detection system comprises an excitation source, a fluorophore, a wavelength filter to isolate emission photons from excitation photons and a detector that registers emission photons and produces a recordable output, in some embodiments as an electrical signal or a photographic image. Examples of detection devices include without limitation spectrofluorometers and microplate readers, fluorescence microscopes, fluorescence scanners (including e.g. microarray readers) and flow cytometers.

In various exemplary embodiments, the binding of the biomarker to the binding ligand is specific or selective, and the binding ligand is part of a binding pair. By "specifically bind" or "selectively bind" or "selective for" a biomarker herein is meant that the ligand binds the biomarker with specificity sufficient to differentiate between the biomarker and other components or contaminants of the test sample.

The term "solid support" or "substrate" refers to any material that can be modified to contain discrete individual sites appropriate for the attachment or association of a capture binding ligand. Suitable substrates include metal surfaces such as gold, electrodes, glass and modified or functionalized glass, plastics (including acrylics, polystyrene and copolymers of styrene and other materials, polypropylene, polyethylene, polybutylene, polycarbonate, polyurethanes, Teflon, derivatives thereof, etc.), polysaccharides, nylon or nitrocellulose, resins, mica, silica or silica-based materials including silicon and modified silicon, carbon, metals, inorganic glasses, fiberglass, ceramics, GETEK (a blend of polypropylene oxide and fiberglass) and a variety of other polymers. Of particular use in the present invention are the ClonDiag materials described below.

Frequently, the surface of a biochip comprises a plurality of addressable locations, each of which comprises a capture binding ligand. An "array location," "addressable location," "pad" or "site" herein means a location on the substrate that comprises a covalently attached capture binding ligand. An "array" herein means a plurality of capture binding ligands in a regular, ordered format, such as a matrix. The size of the array will depend on the composition and end use of the array. Arrays containing from about two or more different capture binding ligands to many thousands can be made. Generally, the array will comprise 3, 4, 5, 6, 7 or more types of capture binding ligands depending on the end use of the array. In the present invention, the array can include controls, replicates of the markers and the like. Exemplary ranges are from about 3 to about 50. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, in one aspect, the invention provides a composition comprising a solid support comprising a capture binding ligand for each biomarker of a biomarker panel. In various embodiments, the capture ligand is a nucleic acid. In various embodiments, the capture binding ligand is an antibody. In various embodiments, the composition further comprises a soluble binding ligand for each biomarker of a biomarker panel.

A number of different biochip array platforms as known in the art may be used. For example, the compositions and methods of the present invention can be implemented with array platforms such as GeneChip® (Affymetrix), CodeLink™ Bioarray (Amersham), Expression Array System (Applied Biosystems), SurePrint microarrays (Agilent), Sentrix® LD BeadChip or Sentrix® Array Matrix (Illumina) and Verigene (Nanosphere).

In various exemplary embodiments, detection and measurement of biomarkers utilizes colorimetric methods and systems in order to provide an indication of binding of a target analyte or target species. In colorimetric methods, the presence of a bound target species such as a biomarker will result in a change in the absorbance or transmission of light by a sample or substrate at one or more wavelengths. Detection of the absorbance or transmission of light at such wavelengths thus provides an indication of the presence of the target species.

A detection system for colorimetric methods includes any device that can be used to measure colorimetric properties as discussed above. Generally, the device is a spectrophotometer, a colorimeter or any device that measures absorbance or transmission of light at one or more wavelengths. In various embodiments, the detection system comprises a light source; a wavelength filter or monochromator; a sample container such as a cuvette or a reaction vial; a detector, such as a photoresistor, that registers transmitted light; and a display or imaging element.

In various exemplary embodiments, a ClonDiag chip platform is used for the colorimetric detection of biomarkers. In various embodiments, a ClonDiag ArrayTube (AT) is used. One unique feature of the ArrayTube is the combination of a micro probe array (the biochip) and micro reaction vial. In various embodiments, where a target sequence is a nucleic acid, detection of the target sequence is done by amplifying and biotinylating the target sequence contained in a sample and optionally digesting the amplification products. The amplification product is then allowed to hybridize with probes contained on the ClonDiag chip. A solution of a streptavidin-enzyme conjugate, such as Poly horseradish peroxidase (HRP) conjugate solution, is contacted with the ClonDiag chip. After washing, a dye solution such as o-dianisidine substrate solution is contacted with the chip. Oxidation of the dye results in precipitation that can be detected colorimetrically. Further description of the ClonDiag platform is found in Monecke S, Slickers P, Hotzel H et al., *Clin Microbiol Infect* 2006, 12: 718-728; Monecke S, Berger-Bächi B, Coombs C et al., *Clin Microbiol Infect* 2007, 13: 236-249; Monecke S, Leube I and Ehricht R, *Genome Lett* 2003, 2: 106-118; Monecke S and Ehricht R, *Clin Microbiol Infect* 2005, 11: 825-833; German Patent DE 10201463; US Publication US/2005/0064469 and ClonDiag, *ArrayTube (AT) Experiment Guideline for DNA-Based Applications*, version 1.2, 2007, all incorporated by reference in their entirety. One of skill in the art will appreciate that numerous other dyes that react with a peroxidase can be utilized to produce a colorimetric change, such as 3,3',5,5'-tetramethylbenzidine (TMB). For information on specific assay protocols, see www.clondiag.com/technologies/publications.php.

In various embodiments, where a target species is a protein, the ArrayTube biochip comprises capture binding ligands such as antibodies. A sample is contacted with the biochip, and any target species present in the sample is allowed to bind to the capture binding ligand antibodies. A soluble capture binding ligand or a detection compound such as a horseradish peroxidase conjugated antibody is allowed to bind to the target species. A dye, such as TMB, is then added and allowed to react with the horseradish peroxidase, causing precipitation and a color change that is detected by a suitable detection device. Further description of protein detection using ArrayTube is found in, for example, Huelseweh B, Ehricht R and Marschall H-J, *Proteomics*, 2006, 6, 2972-2981; and ClonDiag, *ArrayTube (AT) Experiment Guideline for Protein-Based Applications*, version 1.2, 2007, all incorporated by reference in their entirety.

Transmission detection and analysis is performed with a ClonDiag AT reader instrument. Suitable reader instruments and detection devices include the ArrayTube Workstation ATS and the ATR 03.

In addition to ArrayTube, the ClonDiag ArrayStrip (AS) can be used. The ArrayStrip provides a 96-well format for high volume testing. Each ArrayStrip consists of a standard 8-well strip with a microarray integrated into the bottom of each well. Up to 12 ArrayStrips can be inserted into one microplate frame enabling the parallel multiparameter testing of up to 96 samples. The ArrayStrip can be processed using the ArrayStrip Processor ASP, which performs all liquid handling, incubation, and detection steps required in array based analysis. In various embodiments, where a protein is detected, a method of using the ArrayStrip to detect the protein comprises conditioning the AS array with buffer or blocking solution; loading of up to 96 sample solutions in the AS wells to allow for binding of the protein; 3× washing; conjugating with a secondary antibody linked to HRP; 3× washing; precipitation staining with TMB; and AS array imaging and optional data storage.

Those skilled in the art will be familiar with numerous additional immunoassay formats and variations thereof which may be useful for carrying out the method disclosed herein. See generally E. Maggio, *Enzyme-Immunoassay*, (CRC Press, Inc., Boca Raton, Fla., 1980); see also U.S. Pat. Nos. 4,727,022; 4,659,678; 4,376,110; 4,275,149; 4,233,402; and 4,230,767.

In general, immunoassays carried out in accordance with the present invention may be homogeneous assays or heterogeneous assays. In a homogeneous assay the immunological reaction usually involves the specific antibody (e.g., anti-biomarker protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include immunoblotting, immunofluorescence methods, immunoprecipitation, chemiluminescence methods, electrochemiluminescence (ECL) or enzyme-linked immunoassays.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Using any of the methods and compositions described herein, a sample can be assayed to determine levels of a biomarker panel. Thus, in one aspect, the invention provides a method of assaying a sample from a patient to determine concentrations of a biomarker panel in the sample. In some embodiments, the method comprises contacting the sample with a composition comprising a solid support comprising a capture binding ligand or capture probe for each biomarker of a biomarker panel.

The invention further provides kits for use in determining lung health or lung cancer status for a number of medical (including diagnostic and therapeutic), industrial, forensic and research applications. Kits may comprise a carrier, such as a box, carton, tube or the like, having in close confinement therein one or more containers, such as vials, tubes, ampoules, bottles, pouches, envelopes and the like. In various embodiments, the kits comprise one or more components selected from one or more media or media ingredients and reagents for the measurement of the various biomarkers and biomarker panels disclosed herein. For example, kits of the invention may also comprise, in the same or different containers, one or more DNA polymerases, one or more primers, one or more suitable buffers, one or more nucleotides (such as deoxynucleoside triphosphates (dNTPs) and preferably fluorescently labeled dNTPs) and labeling components. The one or more components may be contained within the same container, or may be in separate containers to be admixed prior to use. The kits of the present invention may also comprise one or more instructions or protocols for carrying out the methods of the present invention. The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of biomarkers as provided herein. In various embodiments, the kit comprises a biomarker assay involving a lateral-flow-based point-of-care rapid test with detection of risk thresholds, or a biochip with quantitative assays for the constituent biomarkers.

Methods of Diagnosing and Treating

The compositions and methods of the present invention can be used in the prognosis, diagnosis and treatment of disease in a subject. The invention provides compositions and methods for laboratory and point-of-care tests for measuring biomarkers in a sample from a subject. The invention can be generally applied for a number of different diseases. In exemplary embodiments, the disease is lung cancer.

The biomarkers and biomarker panels disclosed herein can be used in methods to diagnose, identify or screen subjects that have, do not have or are at risk for having disease; to monitor subjects that are undergoing therapies for disease; to determine or suggest a new therapy or a change in therapy; to differentially diagnose disease states associated with the disease from other diseases or within sub-classifications of disease; to evaluate the severity or changes in severity of disease in a patient; to stage a subject with the disease and to select or modify therapies or interventions for use in treating subjects with the disease. In an exemplary embodiment, the methods of the present invention are used to identify and/or diagnose subjects who are asymptomatic or presymptomatic for a disease. In this context, "asymptomatic" or "presymptomatic" means not exhibiting the traditional symptoms or enough abnormality for disease.

In various embodiments, a method of determining a prognosis of a disease in a subject, diagnosing a disease in a subject, or treating a disease in a subject comprises taking a measurement of a biomarker panel in a sample from the subject. In various exemplary embodiments, the biomarker panel consists of two or more of CCNI (Cyclin I)(SEQ ID NO: 1), EGFR (Epidermal growth factor receptor)(SEQ ID NO:2), FGF9 (Fibroblast growth factor 19)(SEQ ID NO: 3), GREB1 protein (SEQ ID NO:4), LZTS (Leucine zipper, putative suppresor I)(SEQ ID NO: 5), BRAF (v-raf murine sarcoma viral oncogene homolog B1 (SEQ ID NO: 6), FRS2 (Fibroblast growth factor receptor substrate 2)(SEQ ID NO: 7), ANXA1 (Annexin A1)(SEQ ID NO: 8), Hp2 (Haptoglobin 2)(SEQ ID NO:8), Chain B, Crystal Structure of the Complex formed between MHc-Like Zinc Alpha2-Glycoprotein and Pro1, *Porphyromonas catoniae, Campylobacter showae, Streptocococcus salivaris, Campylobacter rectus, Veillonella parvula, Kigella oralis.*

The term "disease status" includes any distinguishable manifestation of the disease, including non-disease. For example, disease status includes, without limitation, the presence or absence of disease, the risk of developing disease, the stage of the disease, the progression of disease (e.g., progress of disease or remission of disease over time), the severity of disease and the effectiveness or response to treatment of disease.

A "subject" in the context of the present invention is an animal, preferably a mammal. The mammal can be a human, non-human primate, mouse, rat, dog, cat, horse, or cow, but are not limited to these examples. In various exemplary embodiments, a subject is human and may be referred to as a patient. Mammals other than humans can be advantageously used as subjects that represent animal models of a disease or for veterinarian applications. A subject can be one who has been previously diagnosed or identified as having a disease, and optionally has already undergone, or is undergoing, a therapeutic intervention for a disease. Alternatively, a subject can also be one who has not been previously diagnosed as having a disease. For example, a subject can be one who exhibits one or more risk factors for a disease, or one who does not exhibit a disease risk factor, or one who is asymptomatic for a disease. A subject can also be one who is suffering from or at risk of developing a disease. In certain embodiments, the subject can be already undergoing therapy or can be a candidate for therapy.

As will be appreciated by those in the art, the biomarkers may be measured in using several techniques designed to achieve more predictable subject and analytical variability.

The term "sample" refers to a specimen or culture obtained from a subject and includes fluids, gases and solids including for example tissue. In various exemplary embodiments, the sample comprises saliva. As will be appreciated by those in the art, virtually any experimental manipulation or sample preparation steps may have been done on the sample. For example, wash steps and/or fragmentation may be applied to a sample. In various embodiments, a biomarker panel is measured directly in a subject without the need to obtain a separate sample from the patient.

In one aspect, the invention provides a method of diagnosing a subject for a disease comprising taking a measurement of a biomarker panel; and correlating the measurement with the disease. The term "correlating" generally refers to determining a relationship between one type of data with another or with a state. In various embodiments, correlating the measurement with disease comprises comparing the measurement with a reference biomarker profile or some other reference value. In various embodiments, correlating the measurement with disease comprises determining whether the subject is currently in a state of disease.

The quantity or activity measurements of a biomarker panel can be compared to a reference value. Differences in the measurements of biomarkers in the subject sample compared to the reference value are then identified. In exemplary embodiments, the reference value is given by a risk category as described further below.

In various embodiments, the reference value is a baseline value. A baseline value is a composite sample of an effective amount of biomarkers from one or more subjects who do not have a disease, who are asymptomatic for a disease or who have a certain level of a disease. A baseline value can also comprise the amounts of biomarkers in a sample derived from a subject who has shown an improvement in risk factors of a disease as a result of treatments or therapies. In these embodiments, to make comparisons to the subject-derived sample, the amounts of biomarkers are similarly calculated. A reference value can also comprise the amounts of biomarkers derived from subjects who have a disease confirmed by an invasive or non-invasive technique, or are at high risk for developing a disease. Optionally, subjects identified as having a disease, or being at increased risk of developing a disease are chosen to receive a therapeutic regimen to slow the progression of a disease, or decrease or prevent the risk of developing a disease. A disease is considered to be progressive (or, alternatively, the treatment does not prevent progression) if the amount of biomarker changes over time relative to the reference value, whereas a disease is not progressive if the amount of biomarkers remains constant over time (relative to the reference population, or "constant" as used herein). The term "constant" as used in the context of the present invention is construed to include changes over time with respect to the reference value.

The biomarkers of the present invention can be used to generate a "reference biomarker profile" of those subjects who do not have a disease according to a certain threshold, are not at risk of having a disease or would not be expected to develop a disease. The biomarkers disclosed herein can also be used to generate a "subject biomarker profile" taken from subjects who have a disease or are at risk for having a disease. The subject biomarker profiles can be compared to a reference biomarker profile to diagnose or identify subjects at risk for developing a disease, to monitor the progression of disease, as well as the rate of progression of disease, and to monitor the effectiveness of disease treatment modalities. The reference and subject biomarker profiles of the present invention can be contained in a machine-readable medium, such as but not limited to, analog tapes like those readable by a VCR; optical media such as CD-ROM, DVD-ROM and the like; and solid state memory, among others.

Measurements of the biomarker panels of the invention can lead a practitioner to affect a therapy with respect to a subject. Thus, the invention provides methods of treating a disease in a subject comprising taking a measurement of a biomarker panel in a sample from the subject, and affecting a therapy with respect to the subject. The terms "therapy" and "treatment" may be used interchangeably. In certain embodiments, the therapy can be selected from, without limitation, initiating therapy, continuing therapy, modifying therapy or ending therapy. A therapy also includes any prophylactic measures that may be taken to prevent disease.

In certain embodiments, treatment comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery, for example, mastectomy.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

Drug Treatments

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug.

A number of compounds such as a disease-modulating drug may be used to treat a subject and to monitor progress using the methods of the invention. In certain embodiments, the disease-modulating drug comprises The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more glucose lowering drugs.

Decision Matrices

The therapy chosen by a practitioner can depend on the concentrations of biomarkers determined in a sample. In various exemplary embodiments, the therapy depends on which category from a range of categories particular to each biomarker the measured concentration of each biomarker falls in. In various exemplary embodiments, the therapy depends on the combination of risk levels for different symptoms or diseases that are indicated by a biomarker panel.

With respect to concentration measurements of a biomarker, the term "category" refers to a subset of a partition of the possible concentrations that a biomarker may have. Each category may be associated with a label or classification chosen by the practitioner. The labels may be refer to, for example, the risk level of an individual for having or being subject to a disease state. The categories and labels may be derived from the current literature or according to the findings of the practitioner.

Each biomarker of a biomarker panel can thus be associated with a discrete set of categories, for example, risk categories. Combining one category from each biomarker forms a "decision point." In various exemplary embodiments, the complete set of decision points comprises all possible n-tuples of categories, wherein n is the number of biomarkers in the biomarker panel. This complete set will have $m_1 \times m_2 \times \ldots m_n$ possible decision points, wherein $m_i$ is the number of categories for biomarker i.

Every decision point can be associated with a condition or a disease state, which is not necessarily unique. That is, one or more decision points can be associated with the same disease state. The association of every possible decision point with a condition or disease state can be referred to as a "disease classification matrix" or a "disease classification tree." Thus, by correlating a measurement of a biomarker panel with a decision point, the practitioner can classify the condition or disease state of a patient.

Every decision point can also be associated with a particular therapy, which is not necessarily unique. That is, one or more decision points can be associated with the same therapy. The association of every possible decision point with one or more therapies can be referred to as a "therapy decision matrix" or "therapy decision tree."

Each decision point can be associated with more than one type of information. For example, both disease state and therapy can be indicated by a decision point.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-limiting examples.

EXAMPLES

The following examples are offered to illustrate, but not to limit the invention.

Example 1

Salivary Transciptomic Profiling and Analysis

Saliva Collection

Unstimulated whole saliva samples were collected with previously established protocols. Subjects were asked to refrain from eating, drinking, smoking, or oral hygiene procedures for at least 30 minutes before the collection. Lipstick was wiped off, and the subject rinsed her mouth once with plain water. Typically, patients donated approximately 5-10 ml of saliva. Samples were then centrifuged at 2,600 g for 15 minutes at 4° C. The supernatant was then stored at −80° C. until use. Of note, protease inhibitors cocktail, containing 1 µl aprotinin, 10 µl PMSF (phenylmethanesulfonyl fluoride) and 3 µl sodium orthovanadate (all from Sigma, St. Louis, Mo.) were added to each 1 ml saliva sample.

mRNA Isolation and Analysis

RNA was isolated from 330 µl of saliva supernatant using MagMax™ Viral RNA Isolation Kit (Ambion, Austin, Tex.). This process was automated using KingFisher® mL technology (Thermo Fisher Scientific, Waltham, Mass.), followed by TURBO™ DNase treatment (Ambion, Austin, Tex.) to remove contaminating DNA. 90 µl of extracted RNA (out of 100 µl) was concentrated to 11 µl and was linearly amplified using the RiboAmp® RNA Amplification kit (Molecular Devices, Sunnyvale, Calif.). After purification, cDNA was transcribed and biotinylated using GeneChip® Expression 3'-Amplification Reagents for in vitro transcription labeling (Affymetrix, Santa Clara, Calif.). Approximately 20 µg of labeled RNA were subsequently submitted for GeneChip® analysis using an Affymetrix Human Genome U133 Plus 2.0 Array. Chip hybridization and scanning were performed.

Gene Array Statistical Analysis

The CEL files from all databases were imported into the statistical R 2.7.0 (hypertext transfer protocol://www.r-project.org) using Bioconductor 2.2 (hypertext transfer protocol://www.bioconductor.org. The Probe Logarithmic Intensity Error Estimation (PLIER) expression measures were computed after background correction and quantile normalization for each microarray dataset. Probeset-level quantile normalization was performed across all samples to make the effect sizes similar among all datasets. Finally, for every probeset, two-sample t-test was applied to identify differential expression. After obtaining the estimates and the p-values of each probset, p-values of each probeset was corrected for false discovery rate (FDR). Genes were selected at the FDR level of 0.05, and with cancer effect size >2 fold change between cancer and normal samples.

Screening of Biomarker Candidates

The biomarker candidates generated by microarray profiling were subjected to further screening by real-time quantitative RT-PCR (qPCR) on the same set of samples used for the microarray analysis. To accomplish this, total RNA was reverse-transcribed using reverse transcriptase and genespecific primers using the following thermal cycling conditions: 1 min at 60° C., 30 min at 50° C., 2 min at 95° C., followed by 15 cycles of 15 s at 95° C., 30 s at 50° C., 10 s at 72° C. These steps were followed with a final extension of 5 min. at 72° C. and then cooling to 4° C. The preamplified product was cleaned using ExoSAP-IT (USB Corporation) and diluted ⅟₄₀ in water. 2 μl of the cDNA was used for qPCR.

qPCR was carried out in a 96-well plate in a reation volume of 10 μl using power SYBR®-Green Master Mix (Applied Biosystems, Foster City, Calif.) for 15 min at 95° C. for initial denaturing, followed by 40 cycles of 95° C. for 30 s and 60° C. for 30 s in the ABI 7500HT Fast Real Time PCR system (Applied Biosystems, Foster City, Calif.). All qPCRS were performed in duplicate for all candidate mRNA. The specificity of the PCR was confirmed according to the melting curve of each gene, and the average threshold cycle (Ct) was examined.

Amplicon lengths were around 100-130 bp for the outer primer pairs used in preamplification and 60-80 bp for the inner primer pairs used in qPCR. RT-qPCR primers were designed using Primer Express 3.0 software (Applied Biosystems, Foster City, Calif.). All primers were synthesized by Sigma-Genosys (Woodlands, Tex.), and the amplicons were intron spanning whenever possible.

Raw data were normalized by subtracting GAPDH Ct values from the biomarker Ct values to generate ΔCt. The Mann-Whitney rank sum test was used for between-group biomarker comparisons.

The data analysis for qPCR was performed using the $2^{-Ct}$ method, where GAPDH is used as the reference gene. The qPCR based gene expression values between two groups were compared using the non-parametric Wilcoxon test. To normalize for RNA input, qPCR was also performed for GAPDH. Raw data were normalized by subtracting GAPDH Ct values from the marker Ct values to provide ΔCt and then analyze with the stats, utilities packages from R 2.7.0 (world wide web.r-project.org) and the ROC package from Bioconductor 2.2 (world wide web.bioconductor.org). Statistical comparisons were made with the use of the Mann-Whitney U test with consideration of two different distributions for control and pancreatic cancer groups. Biomarkers that differentiated between groups of subjects (P value <0.05) were identified and compared by Area Under Curve (AUC) value. The AUC is based on constructing a receiver operating characteristic (ROC) curve which plots the sensitivity versus one minus the specificity. The AUC value is computed by numerical integration of the ROC curve. The range of this value can be 0.5 to 1.0. A value of 0.5 indicates that the biomarker is no better that a coin toss, while 1.0 indicates the relatively best diagnostic accuracy.

Seven mRNA biomarkers were identified as differentially expressed between lung cancer subjects and control subjects. The logistic regression model, with the combination of three mRNA biomarkers (GREB1, CCNI, and FRS2) differentiated lung cancer patients from control subjects, yielding a ROC-plot AUC value of approximately 0.91 with approximately 91% sensitivity and approximately 88% specificity.

Example 2

Salivary Proteomic Profiling and Analysis

Protein Isolation and Analysis

Saliva from 10 healthy control subjects and 10 lung cancer subjects were collected and centrifuged at 2600 g at 4° C. for 15 minutes. Saliva supernatant from the 10 health control subjects and 10 lung cancer subjects were pooled to form a control sample and a cancer sample for proteomic profiling. 250 μg of proteins in the pooled saliva samples were precipitated by methanol and then resuspended in 2-D cell lysis buffer (30 mM Tris-HCl, pH 8.8, containing 7M urea, 2M thiourea and 4% CHAPS detergent). The total proteins of each pooled sample, lung cancer and control, were labeled with the cyanine dyes Cy2 and Cy5 respectively. The two labeled sample sets were then combined and subjected to two-dimensional difference gel electrophoresis. After loading the labeled samples, isoelectric focusing (IEF) (pH3-10) was run following the protocol provided by Amersham BioSciences. The IPG strips were rinses in the SDS-gel running buffer before transferring to 13.5% SDS-gels. The SDS-gels were run at 15° C. until the dye front ran out of the gels. Gel images were scanned immediately following the SDS-PAGE using Typhoon TRIO™ (Amersham BioSciences). The fold change of the protein expression levels was obtained from in-gel DeCyder™ analysis.

Spots with fold changes larger than 1.5 on the gel were cut and then were washed multiple times to remove staining dye and other chemicals. Gel spots were dried to absorb maximum volume of digestion buffer. Dried 2D gel spots were rehydrated in digestion buffer containing sequencing grade modified trypsin (Promega, USA). Proteins were digested in-gel at 37° C. overnight. Digested peptides were extracted from the gel with TFA extraction buffer and with shaking. The digested tryptic peptides were desalted using C-18 Zip-tips (Millipore). The desalted peptides were mixed with CHCA matrix (α-cyano-4-hydroxycinnamic acid) and spotted into wells of a MALDI plate for MALDI-TOF MS (ABI4800) identification. Protein identification was based on peptide fingerprint mass mapping (using MS spectra) and peptide fragmentation mapping (using MS/MS spectra). Combined MS and MS/MS spectra were submitted for database search using GPS Explorer software equipped with the MASCOT search engine to identify proteins from primary sequence databases.

Screening of Biomarker Candidates

Four proteins (Annexin A1, Haptoglobin HP2, Interleukin 1 receptor antagonsit, Zinc Alpha2-glycoprotein). Calprotectin was verified by commercial ELISA kit. The distribution of Haptoglobin HP2, Zinc Alpha2-glycoprotein and Calprotectin in the cancer group and control shows significant difference with a p value of 0.00903, 0.05, and 0.048, respectively.

The four proteins identified in the 2-D gel analysis (above) were subjected to Western blot analysis on the original sample set. Reduced protein samples (15 μg total protein per lane) were loaded onto a 10% bis-Tris gel and run at 150V in MES SDS running buffer for one hour. Pre-stained protein standard (Invitrogen) was used to track protein migration. The proteins were transferred to nitrocellulose membrane by using iBlot® (Invitrogen). The membrane was then washed in wash buffer containing 10 mM Tris-HCl, pH 7.6, 150 mM NaCl, and 0.1% (v/v) Tween®-20 (Sigma-Aldrich) before blocking for one hour in wash buffer containing 5% non-fat dry milk. After further washes in wash buffer, the membrane was incubated with primary antibody (mouse anti-Annexin A1 (Abcam), mouse anti-haptoglobin (Lifespan Bioscience), mouse anti-ZAG (Santa Cruz Biotech), mouse anti-actin (Sigma-Aldrich), all according to manufacturers instructions in blocking buffer at room temperature for 2 h. The membrane was then washed before applying the secondary antibody (anti-mouse IgG peroxidase-linked species specific whole antibody from sheep, GE Healthcare) according to manufacturer's instructions for one hour at room temperature. Finally, the membrane was washed and visualized using ECL Plus™ detection kit (GE Healthcare). The signal intensity of the bands was measured using Image J software (NIH, Bethesda, Md., USA). The intensity of a band representing the protein of interest was divided by the intensity of it corresponding β-actin expression on the same blot for normalization.

The ELISA for calprotectin was done according to manufacturers instructions (Cell Sciences). All saliva samples were diluted 100 fold in sample diluent. All samples were loaded in duplicate.

Example 3

Salivary Microbial Biomarkers

Saliva from 10 healthy control subjects and 10 lung cancer subjects were collected and centrifuged at 2600 g at 4° C. for 15 minutes. The supernatant was decanted and the pellet was used for DNA isolation.

DNA was extracted from the pellet using UltraClean® Microbial DNA Isolation Kit (MO Bio Laboratories) following the manufacturer's instructions. Isolated DNA was then submitted to the Forsyth Institute (Cambridge, Mass., USA) for microbe analysis using their Human Oral Microbe Identification Microarray service. Based on the microarray profiles from control and lung cancer subjects, eleven microbes were identified as being differentially present among the two subject groups.

Quantities of bacterial strains in the original DNA samples were determined using real-time PCR. Specific primers were designed for all species and real-time PCR was performed to quantify bacterial quantity between lung cancer samples and control samples. Seven bacteria were identified by real-time PCR as differentially present among the sample groups. Two bacteria, *Porphyromonas catoniae* and *Campylobacter showae*, were identified as being more abundant in lung cancer subject relative to controls.

Example 4

Screening Method

A patient undergoing routine dental care is screened during the visit. For example, a 62 year old female patient, and former smoker, prior to oral exam is asked to provide a saliva sample. A saliva sample is collected and analyzed either at the point of care or is submitted for analysis by a reference laboratory. The saliva sample is tested for the biomarkers of the instant invention and optionally other biomarkers. Results from the analysis are provided to the dental professional and the patient is informed as to whether she has lung cancer.

```
                                       SEQ ID NO: 1
Cyclin I (NM_001237.3)
ccatttcaat agtcgcggga tacttgaact gcaagaacag ccgccgctcc ggcgggctgc tcgctgcatc tctgggcgtc tttggctcgc cacgctgggc agtgcctgcc tgcgcctttc gcaacctcct cggccctgcg tggtctcgag ctgggtgagc gagcgggcgg gctggtaggc tggcctgggc tgcgaccggc ggctacgact attctttggc cgggtcggtg cgagtggtcg gctgggcaga gtgcacgctg cttggcgccg caggctgatc ccgccgtcca ctcccgggag cagtgatgtt gggcaactct gcgccggggc ctgcgacccg cgaggcgggc tcggcgctgc tagcattgca gcagacggcg ctccaagagg accaggagaa tatcaacccg gaaaaggcag cgcccgtcca acaaccgcgg acccgggccg cgctggcggt actgaagtcc gggaacccgc ggggtctagc gcagcagcag aggccgaaga cgagacgggt tgcaccccctt aaggatcttc ctgtaaatga tgagcatgtc accgttcctc cttggaaagc aaacagtaaa cagcctgcgt tcaccattca tgtggatgaa gcagaaaaag aagctcagaa gaagccagct gaatctcaaa aaatagagcg tgaagatgcc ctggctttta attcagccat tagtttacct ggacccagaa aaccattggt ccctcttgat tatccaatgg atggtagttt tgagtcacca catactatgg acatgtcaat tgtattagaa gatgaaaagc cagtgagtgt taatgaagta ccagactacc atgaggatat tcacacatac cttagggaaa tggaggttaa atgtaaacct aaagtgggtt acatgaagaa acagccagac atcactaaca gtatgagagc tatcctcgtg gactggttag ttgaagtagg agaagaatat aaactacaga atgagaccct gcatttggct gtgaactaca ttgataggtt cctgtcttcc atgtcagtgc tgagaggaaa acttcagctt gtgggcactg ctgctatgct gttagcctca aagtttgaag aaatataccc cccagaagta gcagagtttg tgtacattac agatgatacc tacaccaaga aacaagttcc gagaatggag catctagttt tgaaagtcct tacttttgac ttagctgctc caacagtaaa tcagtttctt acccaatact ttctgcatca gcagcctgca aactgcaaag ttgaaagttt agcaatgttt ttgggagaat taagtttgat agatgctgac ccataacctca agtatttgcc atcagttatt gctggagctg cctttcattt agcactctac acagtcacgg gacaaagctg gcctgaatca ttaatacgaa agactggata taccctggaa agtcttaagc cttgtctcat ggaccttcac cagacctacc tcaaagcacc acagcatgca caacagtcaa taagagaaaa gtacaaaaat tcaaagtatc atggtgtttc tctcctcaac ccaccagaga cactaaatct gtaacaatga aagactgcct ttgttttcta agatgtaaat cactcaaagt atatggtgta cagttttttaa cttaggtttt aatttttacaa tcatttctga atacagaagt tgtggccaag tacaaattat ggtatctatt acttttttaaa tggtttttaat ttgtatatct tttgtatatg tatctgtctt agatatttgg ctaattttaa gtggtttttgt taaagtatta atgatgccag ctgtcaggat aataaattga tttggaaaac tttgcaagtc aaatttaact tcttcaggat tttgcttagt aaagaagttt acttggttta ctatataatg ggaagtgaaa agccttcctc
```

-continued

```
taaaattaaa gtaggtttag gaaaacagac cctcaaattc
tgacattcat tttcctaagc aactggatca atttgctgac
ttgggcataa tctaatctaa gcatatctga atacagtatt
cagagataga tacagtagag attccccaga cttttcgct
ctttgtaaaa cctgtttgtt taggttttgc gaggtaaact
caacagaggt tgggagtgga agagggtggg aagcttatat
gcaaattaac agacgagaaa tgctccagaa ggtttattat
tttaaagcac attaaaaaca aaaactatt tttaaaatcc
tgctagattt tataatggat ttgtgaataa aaaatacccca
gggttctcag aatggaataa atatccctt taatagttat
atatacagat atacaactgt tagctttaat tggcagctct
cttctttttt cttcttttca ctggctttt acttggtgct
ttttcttgtt ttgcactggt ggtctgtgtt ctgtgaataa
agcaaagtaa gaatttacta agagtatgtt aagttttgga
ttattgaaat aagaggcatt tcttagtttt ccagtaggat
ctaaaatgtg tcagctatga gtaagactgg catccaagaa
gtttatatta tagatttagg tcctaattt tataaatcac
aaggtaaaaa aatcacagaa cagatggatc tctaatgaaa
aagggatgtc tttttgttta tagtcatgtg gcaagatgag
agtaaaacca gagagcaaac ctctataagt gttgagtata
tgtatacatt tgaaataaac cagaaatttg ttaccttaaa
aaaaaaaaaa a
```

SEQ ID NO: 2
EGFR(NM_005228.3)
```
ccccggcgca gcgcgggcgc agcagcctcc gcccccccgca
cggtgtgagc gcccgacgcg gccgaggcgg ccggagtccc
gagctagccc cggcggccgc cgccgcccag accggacgac
aggccacctc gtcggcgtcc gcccgagtcc ccgcctcgcc
gccaacgcca caaccaccgc gcacggcccc ctgactccgt
ccagtattga tcgggagagc cggagcgagc tcttcgggga
gcagcgatgc gaccctccgg gacggccggg gcagcgctcc
tggcgctgct ggctgcgctc tgcccggcga gtcgggctct
ggaggaaaag aaagtttgcc aaggcacgag taacaagctc
acgcagttgg gcactttga agatcatttt ctcagcctcc
agaggatgtt caataactgt gaggtggtcc ttgggaattt
ggaaattacc tatgtgcaga ggaattatga tctttccttc
ttaaagacca tccaggaggt ggctggttat gtcctcattg
ccctcaacac agtggagcga attcctttgg aaaacctgca
gatcatcaga ggaaatatgt actacgaaaa ttcctatgcc
ttagcagtct tatctaacta tgatgcaaat aaaaccggac
tgaaggagct gcccatgaga aatttacagg aaatcctgca
```

```
tggcgccgtg cggttcagca caaccctgc cctgtgcaac
gtggagagca tccagtggcg ggacatagtc agcagtgact
ttctcagcaa catgtcgatg gacttccaga accacctggg
cagctgccaa aagtgtgatc aagctgtcc caatgggagc
tgctggggtg caggagagga gaactgccag aaactgacca
aaatcatctg tgcccagcag tgctccggc gctgccgtgg
caagtccccc agtgactgct gccacaacca gtgtgctgca
ggctgcacag gccccgga gagcgactgc ctggtctgcc
gcaaattccg agacgaagcc acgtgcaagg acacctgccc
cccactcatg ctctacaacc ccaccacgta ccagatggat
gtgaaccccg agggcaaata cagctttggt gccacctgcg
tgaagaagtg tcccgtaat tatgtggtga cagatcacgg
ctcgtgcgtc cgagcctgtg gggccgacag ctatgagatg
gaggaagacg gcgtccgcaa gtgtaagaag tgcgaagggc
cttgccgcaa agtgtgtaac ggaataggta ttggtgaatt
taaagactca ctctccataa atgctacgaa tattaaacac
ttcaaaaact gcacctccat cagtggcgat ctccacatcc
tgccggtggc atttaggggt gactccttca cacatactcc
tcctctggat ccacaggaac tggatattct gaaaaccgta
aaggaaatca cagggttttt gctgattcag gcttggcctg
aaaacaggac ggacctccat gcctttgaga acctagaaat
catacgcggc aggaccaagc aacatggtca gttttctctt
gcagtcgtca gcctgaacat aacatccttg ggattacgct
ccctcaagga gataagtgat ggagatgtga aatttcagg
aaacaaaaat ttgtgctatg caaatacaat aaactggaaa
aaactgtttg gacctccgg tcagaaaacc aaaattataa
gcaacagagg tgaaaacagc tgcaaggcca caggccaggt
ctgccatgcc ttgtgctccc ccgagggctg ctggggcccg
gagcccaggg actgcgtctc ttgccggaat gtcagccgag
gcagggaatg cgtggacaag tgcaaccttc tggagggtga
gccaagggag tttgtggaga actctgagtg catacagtgc
cacccagagt gcctgcctca ggccatgaac atcacctgca
caggacgggg accagacaac tgtatccagt gtgcccacta
cattgacggc ccccactgcg tcaagacctg cccggcagga
gtcatgggag aaaacaacac cctggtctgg aagtacgcag
acgccggcca tgtgtgccac ctgtgccatc caaactgcac
ctacgatgc actgggccag tcttgaagg ctgtccaacg
aatgggccta agatcccgtc catcgccact gggatggtgg
gggcctcct cttgctgctg gtggtggccc tggggatcgg
cctcttcatg cgaaggcgcc acatcgttcg gaagcgcacg
```

-continued

```
ctgcggaggc tgctgcagga gagggagctt gtggagcctc
ttacacccag tggagaagct cccaaccaag ctctcttgag
gatcttgaag gaaactgaat tcaaaaagat caaagtgctg
ggctccggtg cgttcggcac ggtgtataag ggactctgga
tcccagaagg tgagaaagtt aaaattcccg tcgctatcaa
ggaattaaga gaagcaacat ctccgaaagc caacaaggaa
atcctcgatg aagcctacgt gatggccagc gtggacaacc
cccacgtgtg ccgcctgctg ggcatctgcc tcacctccac
cgtgcagctc atcacgcagc tcatgccctt cggctgcctc
ctggactatg tccgggaaca caaagacaat attggctccc
agtacctgct caactggtgt gtgcagatcg caaagggcat
gaactacttg gaggaccgtc gcttggtgca ccgcgacctg
gcagccagga acgtactggt gaaaacaccg cagcatgtca
agatcacaga ttttgggctg gccaaactgc tgggtgcgga
agagaaagaa taccatgcag aaggaggcaa agtgcctatc
aagtggatgg cattggaatc aatttttacac agaatctata
cccaccagag tgatgtctgg agctacgggg tgaccgtttg
ggagttgatg acctttggat ccaagccata tgacggaatc
cctgccagcg agatctcctc catcctggaa aaggagaac
gcctccctca gccacccata tgtaccatcg atgtctacat
gatcatggtc aagtgctgga tgatagacgc agatagtcgc
ccaaagttcc gtgagttgat catcgaattc tccaaaatgg
cccgagaccc ccagcgctac cttgtcattc aggggatga
aagaatgcat ttgccaagtc ctacagactc caacttctac
cgtgccctga tggatgaaga agacatggac gacgtggtgg
atgccgacga gtacctcatc ccacagcagg gcttcttcag
cagcccctcc acgtcacgga ctcccctcct gagctctctg
agtgcaacca gcaacaattc caccgtggct tgcattgata
gaaatgggct gcaaagctgt cccatcaagg aagacagctt
cttgcagcga tacagctcag accccacagg cgccttgact
gaggacagca tagacgacac cttcctccca gtgcctgaat
acataaacca gtccgttccc aaaaggcccg ctggctctgt
gcagaatcct gtctatcaca atcagcctct gaaccccgcg
cccagcagag acccacacta ccaggacccc cacagcactg
cagtgggcaa ccccgagtat ctcaacactg tccagcccac
ctgtgtcaac agcacattcg acagccctgc ccactgggcc
cagaaaggca gccaccaaat tagcctggac aaccctgact
accagcagga cttctttccc aaggaagcca agccaaatgg
catctttaag ggctccacag ctgaaaatgc agaataccta
agggtcgcgc cacaaagcag tgaatttatt ggagcatgac
cacggaggat agtatgagcc ctaaaaatcc agactctttc
```

-continued

```
gatacccagg accaagccac agcaggtcct ccatcccaac
agccatgccc gcattagctc ttagacccac agactggttt
tgcaacgttt acaccgactagccaggaagt acttccacct
cgggcacatt ttgggaagtt gcattccttt
gtcttcaaactgtgaagcat ttacagaaac gcatccagca
agaatattgt cccttttgagc agaaatttat ctttcaaaga
ggtatatttg aaaaaaaaaa aaagtatatg tgaggatttt
tattgattgg ggatcttgga gttttcatt gtcgctattg
attttactt caatgggctc ttccaacaag gaagaagctt
gctggtagca cttgctaccc tgagttcatc caggcccaac
tgtgagcaag gagcacaagc cacaagtctt ccagaggatg
cttgattcca gtggttctgc ttcaaggctt ccactgcaaa
acactaaaga tccaagaagg ccttcatggc cccagcaggc
cggatcgta ctgtatcaag tcatggcagg tacagtagga
taagccactc tgtcccttcc tgggcaaaga agaaacggag
gggatggaat tcttccttag acttactttt gtaaaaatgt
ccccacggta cttactcccc actgatggac cagtggtttc
cagtcatgag cgttagactg acttgtttgt cttccattcc
attgttttga aactcagtat gctgcccctg tcttgctgtc
atgaaatcag caagagagga tgacacatca ataataact
cggattccag cccacattgg attcatcagc atttggacca
atagcccaca gctgagaatg tggaatacct aaggatagca
ccgcttttgt tctcgcaaaa acgtatctcc taatttgagg
ctcagatgaa atgcatcagg tcctttgggg catagatcag
aagactacaa aaatgaagct gctctgaaat ctcctttagc
catcacccca acccccaaa attagtttgt gttacttatg
gaagatagtt ttctcctttt acttcacttc aaaagctttt
tactcaaaga gtatatgttc cctccaggtc agctgccccc
aaaccccctc cttacgcttt gtcacacaaa aagtgtctct
gccttgagtc atctattcaa gcacttacag ctctggccac
aacagggcat tttacaggtc gaatgacag tagcattatg
agtagtgtgg aattcaggta gtaaatatga aactagggtt
tgaaattgat aatgctttca caacatttgc agatgtttta
gaaggaaaaa agttccttcc taaaataatt tctctacaat
tggaagattg gaagattcag ctagttagga gcccacccttt
tttcctaatc tgtgtgtgcc ctgtaacctg actggttaac
agcagtcctt tgtaaacagt gttttaaact ctcctagtca
atatccaccc catccaattt atcaaggaag aaatggttca
gaaatatttt tcagcctaca gttatgttca gtcacacaca
catacaaaat gttccttttg cttttaaagt aattttgac
```

-continued tcccagatca gtcagagccc ctacagcatt gttaagaaag tatttgattt ttgtctcaat gaaaataaaa ctatattcat ttccactcta aaaaaaaaaa aaaaaa

SEQ ID NO: 3
FGF19 (NM_002010.2)

actctgcgcg ccggcggggg ctgcgcagga ggagcgctcc gcccggctac aacgctccgc gagccgcgcg ggcaacacct gttcgcggca gcctgggcgg cacgcgagct cccggacgcg gctctcctcg ctcgccgctc gccacccgtt ctaagccaat ggacatctgc cgagcctctg gagaatcctg gatactagct ttggacgcct aaagtttctt cttctttttg ttttattatt attatcattt tttggagggg ggaccgggag gggagatttg tcgccgccac caacgtgaga ttttttttttc cccttgaagg attcatgctg atgtctgcag agtcggttag agagtaaaaa cagcgcatgc cttcctggag tcaggatccg taaattctga cgtagcccgt gcatcttaaa aatccctata ataacgccta ggcatttaag ttgctatggt cattctgatc tcaaaccaaa tggagaaact acggattttt tttccttatt acggtcggat gggatgaaga ccttcctgcc tgctaagagc tggggatcta tctatagaga tacatagata tgtttatcaa tatgtcagtg tgtgagtata aagtggtggt ttcttagact atcagtggtt tgaccttgaa cctgtgccag tgaaacagca gattactttt atttatgcat ttaatggatt gaagaaaaga acctttttt tctctctctc tctgcaactg cagtaaggga ggggagttgg atatacctcg cctaatatct cctgggttga caccatcatt attgtttatt cttgtgctcc aaaagccgag tcctctgatg gctcccttag gtgaagttgg gaactatttc ggtgtgcagg atgcggtacc gtttgggaat gtgcccgtgt tgccggtgga cagcccggtt ttgttaagtg accacctggg tcagtccgaa gcagggggc tccccagggg acccgcagtc acggacttgg atcatttaaa ggggattctc aggcggaggc agctatactg caggactgga tttcacttag aaatcttccc caatggtact atccagggaa ccaggaaaga ccacagccga tttggcattc tggaatttat cagtatagca gtgggcctgg tcagcattcg aggcgtggac agtggactct acctcgggat gaatgagaag ggggagctgt atggatcaga aaaactaacc caagagtgtg tattcagaga acagttcgaa gaaaactggt ataatacgta ctcatcaaac ctatataagc acgtggacac tggaaggcga tactatgttg cattaaataa agatgggacc ccgagagaag ggactaggac taaacggcac cagaaattca cacattttt acctagacca gtggacccg acaaagtacc tgaactgtat aaggatattc taagccaaag ttgacaaaga cagtttcttc acttgagccc ttaaaaaagt aaccactata aaggtttcac gcggtgggtt cttattgatt cgctgtgtca tcacatcagc tccactgttg ccaaactttg tcgcatgcat aatgtatgat ggaggcttgg atgggaatat gctgattttg ttctgcactt aaaggcttct cctcctggag ggctgcctag ggccacttgc ttgatttatc atgagagaag aggagagaga gagagactga gcgctaggag tgtgtgtatg tgtgtgtgtg tgtgtgtgtg tgtgtgtgta tgtgtgtagc gggagatgtg ggcggagcga gagcaaaagg actgcggcct gatgcatgct ggaaaaagac acgcttttca tttctgatca gttgtacttc atcctatatc agcacagctg ccatacttcg acttatcagg attctggctg gtggcctgcg cgagggtgca gtcttactta aaagactttc agttaattct cactggtatc atcgcagtga acttaaagca aagacctctt agtaaaaaat aaaaaaaaat aaaaaataaa aataaaaaaa gttaaattta tttatagaaa ttccaaaggc aacattttat ttattttata tatttattta ttatatagag tttattttta atgaaacatg tacaggccag ataggcattt tggaagcttt aggctctgta agcattaaat ggcaaagtcc gctatgaacc tgtggtaaat tcatgcaagt agatataatg gtgcatggat ataagaaatt ctaatgaccc taatgtacta aaggcgacaa tctcttttgt gcccatatta ttgtaaactt atgcacatcg ctcatgacac tgagtattca ctcttcagac tgcttgtttc atagcttatc ccagaggatt aaagataaac tgggtctcaa actttgattc tgtgtctgca atatttcctc tctcataagt gactccacta ttgtaacttc atggttggaa aatatgaggg ttgatatatg tcttacttgt ttaaatctgt cgcagaatat accaaagcta aataataact atgctttcat tttagccgat ctccagaatg acagtattaa catcaaacat tgtattgatt tagaattctc aaaaaaggaa aaaaagtac atagcacaga ctatttttt taaagactgta agaatcagat taacaggatc atacttgtaa acttttttg gttcacttgg ctatcaaata tgaaattata gaagtatcat aggggtcatt gtaacatctt ttagagaaaa tggctatcag tgtgaactgt cataattacg tggtaatag accttagta aaacttgcaa aatgaaacta ataaatcgtt atcaataatg acaatgaggg ggaaagtatt atacttgttg actgtgtttt gttttttaaa atggtctcca caagcgctca atttttttag aggggatatt actatataga atatctttta caaggctttt ataacatttt atgctgaaaa gcataagaat acgtatttct ttagtagcaa taattttgga acttgcccct gggcaagcga gactattcct -continued

```
tactatatac taaggagaaa agagccaaat tcttaaagca
atatttaaga aaaaaggaat ttataacaaa ttctcatcta
catatgacac tttctagcca gttgtgttga gaagtgcaaa
gtgacggttt aaacatgtgt tgggatttat tgaactaatt
ttaaaattta ctattcaaac tttattttgc tctgatgcac
attctctatg aaaaataaaa gtgtgtcact ggtgagtgac
agctgttatg agctagaagc gcatgactta ttgtgacgat
gtcttgcctt tctgtggtcc aagttggagt acatggcaat
gccctcctgc tgatgtgcat taaggaaaat ctaagtctaa
tatttggaat taagatatat tttaggggga gggacagaa
gcaatgtaaa atagttgatt tatgataaag ctcagaatgt
cctcttcatt tattttcttg ttttattttc ctttctaaac
agaaactgca tttaattcca aaaagtagta ttcttattta
ttatttaacc ctttgctgct gctaaaatgt gcacatattc
aggctttagt ttttccaaaa ggcatttttt ttttggctga
aaaatattaa acatttgacc acagggaaga atcaagtttc
taggatgtca taggtatact atgtagcact gaaaaaattg
attttaggtg acagccaaaa gtagtcttaa agtagcatga
gaccttagat aatcgaccta aaagaaagaa aattgtgaaa
aagacaaaaa tcttcatgca ttcctataaa acgctacttt
aaggtctact tttggagtta attttgtttg gtactttttt
ttttttaag acgagcaaat tgttatatgc ttttggcaat
tgatacaata aactgtaatg gtctgtaaat aaataaatat
tgactcatgc gatttatgta aatagtggaa ctgggagagt
ggatggctca gggtttcggt gtgggcattg tctcttgggc
agtagagtga gtcatcccca gctcatgggt ttgcatccag
ttcttgtctt aagagaccca agcccagtga aatggcagcc
ctgagccact gtggaatggg ggttctggtt tcacaaacag
atgcttagat agccaaacca ctgtcttgtt ggtgccaaca
cttgcactgt ggtcaaagac ttaccgagca tgggctgaac
aaccttccca tctgtcatgt gaatgtcccc aagcagtggt
gaaggacatg ctaggtcagt gttggggaac ctgccctgcc
aggtcctgtt ttgtagataa acaaatggct gccttctggt
gtttttattc tatttcatct cattaacact acaaccttgt
gttatttact tgataatctg taattgtatg taaatacata
caggattatg taatttgtgt aaatacataa ttacagagtt
ttgaaaactg aaaaaaaaaa aaaaa
```

SEQ ID NO: 4
GREB1 (NM_033090.2)
```
gaaagaatca aagcgcacat cttgtacttt gatgcccata
ggaagggctc tcctctggcc cctctggctt tgtttggagc
agaaaacaac aaactgcagc tgaggacagc cacccttcct
tcgtctctgc tgagcgaagg ctacacggcc cttcctcctt
gcagctgttt caccttctac cttgcgtgga gccaggcttt
tgcaccgaat ctgagatgcc atttaaaca gaagactcca
tcctcttgaa gatgggaaat tcttacgctg gacagctgaa
gacgacacg tttgaagagg tcttgcacaa ttccatcgag
gcatccctgc ggtccaacaa cctggtgccc aggcccatct
tttcccagct gtacctggaa gctgagcagc agcttgccgc
tctagaaggt ggtagccgag tggacaatga ggaagaggaa
gaagagggag aaggagggct ggaaacaaat ggccccccaa
accctttcca gctgcaccct ctgcctgaag gatgctgtac
cacagacggg ttttgccagg ccgggaagga cctgcgcctt
gtctccattt ccaacgagcc catggatgtc cctgcgggct
ttctcctcgt gggggtcaag tcccccagcc tgccggacca
tctcctggtg tgcgccgtta caagaggtt cttgccagat
gacaatggcc acaatgctct tcttggtttc tctgggaatt
gtgttggctg tggaaagaaa ggcttctgtt acttcacgga
attctccaat catataaatc tgaaactgac cactcaaccc
aagaagcaga aacacttgaa gtattacctg gtccgtaatg
cacaagggac tctaaccaaa ggacctttaa tctgttggaa
aggctcagag tttagaagcc ggcagatccc cgccagtact
tgttccagtt ccctcttccc agccctggag agcacggct
ccttcccag cgagcccgtt cctgggacga accccagcat
cctgatggga gctcagcagg caggaccagc ttctgatcac
ccctcactaa acgcagcaat gggtccggct gttttcaacg
gcaaagattc cccgaagtgc caacaactgg caaagaataa
cctgttggcc ctgccgcgac catcggcttt aggtatcttg
tcaaactccg ggcccccaa aaaacgccac aaagggtggt
ctccagaatc tccatcagct ccagatggtg gctgccccca
aggtggtggg aacagagcta agtatgagag cgcaggcatg
tcctgcgtgc cgcaggttgg cttggtggga ccagcttcag
tcacctttcc agtggtggcc tctggagaac cagtgtctgt
tcctgacaac ttgctgaaaa tatgcaaggc caagccagtg
atatttaaag gccatgggaa cttcccttac ctctgtggga
acctgaatga cgtcgtggtc agccccctct tgtacacgtg
ctaccagaat tcccagtctg tctcacgggc atacgagcag
tacggcgcct ctgccatcca gccatctccc gaggagatgc
agctcctgct taccgtctac tacctggtcc agctggcaca
tcaaatacga aatccggacg tataaaccag acaattcata
aaagagaaaa taccagaagg aaacaaatat tgaaaagtat
tcagtctcac tcatcatcaa agacatgcaa atcacaaatc
```

-continued aagtcatctt tttctgaatt aataacccaa atgatggtac
ccagtggtgc ttaggtgcgg taaaaccagc gcttgtccga
tgcaccgttc gcgtggtaaa ctgacgcatt caggctcttg
ggaagcaatc tgatgatatg tagtagctgc ttctgtaaat
ccacctttga gaatttaggc gaaggaagta acgttctata
tgtcaagatg tgcattgcag agggatttat aaaggtgaat
atttggaaga aataagagaa tccacaatag agaccttgct
aagtaaacgg tggtgctcac gtatgatggg acattatgga
cacactaaca gcactcttta tgttggctga aaatggcact
gaaactgatg ataggtcat ggttaaggaa agaatgcaag
acccaaagtt tatactgaca atcattgcag ctatttgtaa
ggacagtttt aatactaatt ccagcaatac atgtttttat
tccctgtcct ggagtaggag aaagcctata ttcccaggct
gaatgttcta cacatttacc actgtatatg cataggga
cagtgtaacc tgtctatacc accgtagttc cagtcctaac
tttctgaatt ctgtttaaag accttct SEQ ID NO: 5
LZTS1 (NM_021020.2)
tgagggcttt gctatgacct cagtcccctc acggagccac
gactgcccct tgctgccaca gccttccaa gaccctgccc
ggccctgccc catcctcagc ccgagtcac catgggcagc
gtcagtagcc tcatctccgg ccacagcttc cacagcaagc
actgccgggc ttcgcagtac aagctgcgca gtcctccca
cctcaagaag ctcaaccggt attccgacgg gctgctgagg
tttggcttct cccaggactc cggtcacggc aagtccagct
ccaaaatggg caagagcgaa gacttcttct acatcaaggt
cagccagaaa gcccggggct cccatcaccc agattacacg
gcactgtcca gcgggatttt agggggccag gctggggtgg
actttgaccc gtccacaccc cccaagctca tgcccttctc
caatcagcta gaaatgggct ccgagaaggg tgcagtgagg
cccacagcct tcaagcctgt gctgccacgg tcaggagcca
tcctgcactc ctcccgggag agtgccagcc accagctgca
ccccgcccct ccagacaagc caaggagca ggagctgaag
cctggcctgt gctctgggc gctgtcagac tccggccgga
actccatgtc cagcctgccc acacacagca ccagcagcag
ctaccagctg gacccgctgg tcacacccgt gggacccaca
agccgttttg ggggctccgc ccacaacatc acccagggca
tcgtcctcca ggacagcaac atgatgagc tgaaggctct
gtccttctcc gacggaggta gcaagctggg ccactcgaac
aaggcagaca agggcccctc gtgtgtccgc tcccccatct
ccacggacga gtgcagcatc caggagctgg agcagaagct -continued gttggagagg gagggcgccc tccagaagct gcagcgcagc
tttgaggaga aggagcttgc ctccagcctg gcctacgagg
agcggccgcg gcgctgcagg gacgagctgg agggcccgga
gcccaaaggc ggcaacaagc tcaagcaggc ctcgcagaag
agccagcgcg cgcagcaggt cctgcacctg caggtactgc
agcttcagca ggagaagcgg cagctccggc aggagctcga
gagcctcatg aaggagcagg acctgctgga gaccaagctc
aggtcctacg agagggagaa gaccagcttc ggccccgcgc
tggaggagac ccagtgggag gtgtgccaga gtcaggcga
gatctccctc ctgaagcagc agctgaagga gtcccagacg
gaggtgaacg ccaaggctag cgagatcctg ggtctcaagg
cacagctgaa ggacacgcgg ggcaagctgg agggcctgga
gctgaggacc caggacctgg agggcgccct cgcaccaag
ggcctggagc tggaggtctg tgagaatgag ctgcagcgca
agaagaacga ggcggagctg ctgcgggaga aggtgaacct
gctggagcag gagctgcagg agctgcgggc ccaggccgcc
ctggcccgcg acatggggcc gccaccttc cccgaggacg
tccctgccct gcagcgggga ctggagcggc tgcgggccga
gctgcgggag gagcggcaag gccatgacca gatgtcctcg
ggcttccagc atgagcggct cgtgtggaag gaggagaagg
agaaggtgat tcagtaccag aaacagctgc agcagagcta
cgtggccatg taccagcgga accagcgcct ggagaaggcc
ctgcagcagc tggcacgtgg ggacagcgcc ggggagccct
tggaggttga cctggaaggg gctgacatcc cctacgagga
catcatagcc actgagatct gaggggctgc ctgggaaggc
gagtctgggg acctggcact gggaggcagg gctctcccgt
gcatcccccc tgctcagcaa ttcagacccc tttgagagac
gccactccct gggacacaga cccaggaccc ccgaggggag
ggcaggatgg cctttccttc cctctctgat gtcccagtgc
tcaccagccc tgcagccac cagacgtcag gccctgactc
ctctggcttt cccaggagat gggtccaggg gtctgtctgc
tttggttaag ggctccctaa actttggcct ttgttcgaaa
tagatatcct ctccccctcc tccagggaag gtggccacag
caagtacagc ggctcccctc tgcttctcat cccaacctct
tttcctcct ggacacattg gaatgccttg gaaatagaaa
gaagccatat atgaccgaaa gccttggaac cagccccatc
agaacctgag ctatttcct ctggccgcag aggtgtagg
gtggaatgag ccgcggggaa gctggctttg aaacctcagg
gctgtcccag ccccggcaag ccacaggaag gaggggagag
acaggcagcc cagcagtgtg agaccctgc cacagccaga
ggagggcaga gggagaatcc aagggttgag agccagtggc -continued gggtgatggc cagcccctgg ggcccagccc ctgtttactg
gttcttgcaa atgggagctg agcagcctct ggacagccag
tgacctttga cctcggtgac cactcttctt taagccatag
accctgaggc cctgggctgg gtgctgggaa gggaggggttg
aaaccaccgt gaaccagagg gtgtggcttt ccaggcaccc
tcagggagcc tccccatctg tccagctggg gccagaggct
gggagtccct acctgcttca cgttggccgg cggctactct
ggaatgtttt tccctcccca gaatcaagct tttgcttgat
ccagaagagc ccatatcact aagatggcat atatgtgatc
tgggcatttt cctcctctgc ctacagccag gtttagcggc
aaacctttcc cccttagcac cttcagggct gagttctggg
tttctagagg tcaggacggc tcctcagagc gccaggaagc
cagagcccca agcaggacga aaaagaggca tacacacagc
agtgtgaata gcctggccac cagccatcct ccctccacct
caagacccc atttgtccca gactaaagga tccagagagc
agctcccttt ctcaggagct tgggcagtgc cccagggagt
ccagggtttc tctgcagatg tgcggagcgg gaggcggtgg
tagagagaga taaaaggtgg agtttctctg ttgtttggtt
cagggatttt atttttaatt ttatgagaca gggtcttgct
ctgtcccca ggctggagtg cagtggcatg atcatagctc
actgcagcct catactcctg ggctcaagca atcctcctgc
ctcagcccttc caactagctg ggactacagg tgcgcgccac
cgtgcctggc taacttttca tttttttgt agggacgggg
tctcgttttg ttgccaaagc tggtctcaaa cttgtggcct
caagcaatcc acctgccttg gcctcccaaa gtgctgagat
tgcagatgtg agccaccgtg cctggccaga ttttttctttt
attcttcttt cttttctttt tttgcttct tgtcttttca
gaagcaagcc agacctagca ggctgttcca tgttctattt
ttgactgtag ccacagctgc tgttctcagg acagcatccc
ttcccacatg cctgcgcctg ctgcctgctg agatgaggag
gggagcgtct gggaacttgc gagtccaagg ccagtcccca
tttctgcctc gctcaccgct ggcccttaga gaccccgagg
tagggggtggg gagatgcttc tctccttgcc cccgccctc
atgggtccta gcccttccct gagtgcgggc tgaggccaga
gtcaccttt ctgtggctgg ctctaccttc ctgtcccctga
ggttaaacgg tgcccatcct gccatcctca aacgacagag
gagcttttct ggaatttcaa accattgctc ttagtcccaa
gctaggctta aacctggaat ctacaagcca aaagtccctc
cctgcctgag ggcagtaccc tccattggg acagtccaga
cccaagtcaa agatgcccca ttccttgcgc ctcagcccctc agttccttca tttccaccag gccgtgcctt gtttgagttt
ttcctcccag tgagactgcc ccacggagac agaggaaagg
gctggctccc cctccccagg ctggagaccc cccccaact
ccaggaaaga gcagtcagag tccagtgctc tgcctcagac
gttgcctgag aagaagtggc tgccacaccc aggggaaggc
cctgaggcgg aggctgtgct ccgccatggt gtcccggtac
cttccataca cagaggagtg cagccttctc catatctcc
tggccctgtc ccaggccggc ccagatgtgt cccccccagg
ccttgtccta cgtccaaggt ggcagatgtc ttccctgggc
tgccaccagc ccccgcccca gagtggccca ccgtggcact
agaatgcaag tatcctgcga ccttgcaacc tcaccttcct
gtgggtgttc tttcctgccc tgtccaaaag cgccctcact
attcttgac catgccagat tctgcctctc tggaaagagg
ctctggacag cagaagcctc caagcacaga gcctggcccc
aggcccccaga cagggtgggc ttcctgccct tccctctggg
cacgcctgct ggccgaccca ctgacccact cggatggacc
aacctgctct gtccccaaag gacgcctgca ggagagagca
gcactccgca tcacctcacc aaggatcgga ctctgcccct
ggacctggga acgactggac tgtcacgggg ttccctccta
gctctcccag tgaactcctg ccaggcacac acagcccta
tagcactgag ctcacatggg actgggatat gggggcatct
cttccccaga gaggcactca gtgagcctcc tgtgcctggc
cccagcctgg gccatctctt aggtgagaca gttgcccgaa
actaagccag gcctggctgg aggagcagca gcttggggag
agggatttcc ctgcagacct caagccatca tgcggtgggt
gctgccatga cagaggctgc acccctgggc cagcgggggct
gctcacccac ctcttgtgca aggtggcctt tgtgctgcgc
ctgcaggcag agctggagcc cccagcagag gcaggctggg
acggaccagc atctggaaga tgtacatagt tattttttctc
tttgtggttt cttgtttggt ttggtttgct tttgacagct
tcatttttatt tttgacgtca cttttttggcc atgtaaacta
tttgtggcaa ttttatgttt ttatttatga ataaagaatg
ccatttctca cgccctcta SEQ ID NO: 6
BRAF (NM_004333.4)
cgcctccctt cccctcccc gcccgacagc ggccgctcgg
gccccggctc tcggttataa gatggcggcg ctgagcggtg
gcggtggtgg cggcgcggag ccgggccagg ctctgttcaa
cggggacatg gagcccgagg ccggcgccgg cgccggcgcc
gcggcctctt cggctgcgga ccctgccatt ccggaggagg
tgtggaatat caaacaaatt attaagttga cacaggaaca
tatagaggcc ctattggaca aatttggtgg ggagcataat

```
ccaccatcaa tatatctgga ggcctatgaa gaatacacca
gcaagctaga tgcactccaa caaagagaac aacagttatt
ggaatctctg gggaacggaa ctgattttc tgtttctagc
tctgcatcaa tggataccgt tacatcttct tcctatcta
gcctttcagt gctaccttca tctctttcag tttttcaaaa
tcccacagat gtggcacgga gcaaccccaa gtcaccacaa
aaacctatcg ttagagtctt cctgcccaac aaacagagga
cagtggtacc tgcaaggtgt ggagttacag tccgagacag
tctaaagaaa gcactgatga tgagaggtct aatcccagag
tgctgtgctg tttacagaat tcaggatgga gagaagaaac
caattggttg gacactgat atttcctggc ttactggaga
agaattgcat gtggaagtgt tggagaatgt tccacttaca
acacacaact tgtacgaaa acgtttttc accttagcat
tttgtgactt ttgtcgaaag ctgcttttcc agggtttccg
ctgtcaaaca tgtggttata aatttcacca gcgttgtagt
acagaagttc cactgatgtg tgttaattat gaccaacttg
atttgctgtt tgtctccaag ttctttgaac accacccaa
accacaggaa gaggcgtcct agcagagac tgccctaaca
tctggatcat cccttccgc accgcctcg gactctattg
ggccccaaat tctcaccagt ccgtctcctt caaaatccat
tccaattcca cagcccttcc gaccagcaga tgaagatcat
cgaaatcaat tgggcaacg agaccgatcc tcatcagctc
ccaatgtgca tataaacaca atagaacctg tcaatattga
tgacttgatt agagaccaag gatttcgtgg tgatggagga
tcaaccacag gtttgtctgc tacccccct gcctcattac
ctggctcact aactaacgtg aaagccttac agaaatctcc
aggacctcag cgagaaagga agtcatcttc atcctcagaa
gacaggaatc gaatgaaaac acttggtaga cgggactcga
gtgatgattg ggagattcct gatgggcaga ttacagtgg
acaaagaatt ggatctggat catttggaac agtctacaag
ggaaagtggc atggtgatgt ggcagtgaaa atgttgaatg
tgacagcacc tacacctcag cagttacaag ccttcaaaaa
tgaagtagga gtactcagga aaacacgaca tgtgaatatc
ctactcttca tgggctattc cacaaagcca caactggcta
ttgttaccca gtggtgtgag ggctccagct tgtatcacca
tctccatatc attgagacca aatttgagat gatcaaactt
atagatattg cacgacagac tgcacagggc atggattact
tacacgccaa gtcaatcatc cacagagacc tcaagagtaa
taatatattt cttcatgaag acctcacagt aaaaatagg
gattttggtc tagctacagt gaaatctcga tggagtgggt
```

```
cccatcagtt tgaacagttg tctggatcca ttttgtggat
ggcaccagaa gtcatcagaa tgcaagataa aaatccatac
agctttcagt cagatgtata tgcatttgga attgttctgt
atgaattgat gactggacag ttaccttatt caaacatcaa
caacagggac cagataattt ttatggtggg acgaggatac
ctgtctccag atctcagtaa ggtacggagt aactgtccaa
aagccatgaa gagattaatg gcagagtgcc tcaaaaagaa
aagagatgag agaccactct ttccccaaat tctcgcctct
attgagctgc tggcccgctc attgccaaaa attcaccgca
gtgcatcaga accctccttg aatcgggctg gtttccaaac
agaggatttt agtctatatg cttgtgcttc tccaaaaaca
cccatccagg caggggata tggtgcgttt cctgtccact
gaaacaaatg agtgagagag ttcaggagag tagcaacaaa
aggaaaataa atgaacatat gtttgcttat atgttaaatt
gaataaaata ctctctttt ttttaaggtg aaccaaagaa
cacttgtgtg gttaaagact agatataatt tttccccaaa
ctaaaattta tacttaacat tggatttta acatccaagg
gttaaaatac atagacattg ctaaaaattg gcagagcctc
ttctagaggc tttactttct gttccgggtt tgtatcattc
acttggttat tttaagtagt aaacttcagt ttctcatgca
acttttgttg ccagctatca catgtccact agggactcca
gaagaagacc ctacctatgc ctgtgtttgc aggtgagaag
ttggcagtcg gttagcctgg gttagataag gcaaactgaa
cagatctaat ttaggaagtc agtagaattt aataattcta
ttattattct taataatttt tctataacta ttttcttttta
taacaatttg gaaaatgtgg atgtcttta tttccttgaa
gcaataaact aagtttcttt ttataaaaa
```

SEQ ID NO: 7
FRS2 (NM_006654.3)
```
aaaacccttc cctcccccgc tcccccggaa gtgcttttcc
aagattcggg ccggagagag gccttgtagg cacagcggct
gagactcgat ctgctccaag taggggctcc agcgcgggtc
ggagtctggg ggttcgcgcc cgccgacccg cgccctgctc
cctctcagca cctgggcgga cgaaatgacc attaagaagt
agatgcccag atgcaaaagt gatgaaacag tccatttgtc
ataaagtaag atgcagctgt ggcatgtcaa ccagcttgga
acaaaattgt atctgttttt ctcagaagag aattccacaa
ggagattttc ttctttctac catcatcaag atcaagcagg
caagtttact tgctgtcatc ttctgcaagg ttaaatcagc
aaacaaagaa aacatggtat tttgaaatat gattaaactc
ctgatgctgc agcagaggct aagaatatta atggccagat
ctagtgcaca catggtcttc tgaagaagcc atgggtagct
```

-continued

```
gttgtagctg tccagataaa gacactgtcc cagataacca
tcggaacaag tttaaggtca ttaatgtgga tgatgatggg
aatgagttag gttctggcat aatggaactt acagacacag
aactgatttt atacacccgc aaacgtgact cagtaaaatg
gcactacctc tgcctgcgac gctatggcta tgactcgaat
ctccttttctt ttgaaagtgg tcgaaggtgt caaactggac
aaggaatctt tgcctttaag tgtgcccgtg cagaagaatt
atttaacatg ttgcaagaga ttatgcaaaa taatagtata
aatgtggtgg aagagccagt tgtagaaaga aataatcatc
agacagaatt ggaagtccct agaacacctc gaacacctac
aactccagga tttgctgctc agaacttacc taatggatat
ccccgatatc cctcatttgg agatgcttca tcccatccgt
caagcagaca tccttctgtg ggaagtgctc gcctgccttc
agtaggggaa gaatctacac atcctttgct tgtggctgag
gaacaagtac ataccttatgt caacactaca ggtgtgcaag
aagagcggaa aaaccgcaca agtgtgcatg ttccattgga
ggcgagggtt tctaacgctg aaagcagcac accaaaagaa
gaaccaagta gtattgagga cagggatcct cagattcttc
ttgaacctga aggagtcaaa tttgttttag ggccaacccc
tgttcaaaag cagttaatgg aaaaagagaa actggagcaa
cttggaagag atcaagttag tggaagtgga gcaaataaca
cagaatggga cactggctat gacagtgatg aacgaagaga
tgcaccctct gttaacaaac tggtgtatga aaatataaat
gggctatcta tccctagtgc ctcaggggtc aggagaggtc
gtctgacatc caccagtacc tcagatccc agaatatcaa
caactcagct cagagaagaa ctgcattatt aaactatgaa
aatctaccat ctttgcctcc tgtttgggaa gcccgcaagc
taagtaggga tgaagatgac aatttaggac caaagacccc
atctctaaat ggctaccata ataatctaga tccaatgcat
aactatgtaa atacagagaa tgtaacagtg ccagcaagtg
ctcacaaaat agaatattca aggcgtcggg actgtacacc
aacagtcttt aactttgata tcagacgccc aagtttagaa
cacaggcagc ttaattacat acaggttgac ttggaaggtg
gcagtgactc tgacaaccct cagactccaa aaacgcctac
aactccccctt ccacaaaccc taccaggcg cacagagctg
tatgccgtga tagacatcga gagaactgct gctatgtcaa
atttgcagaa agcactgcca cgagatgatg gtacatctag
gaaaactaga cacaatagta ctgatctgcc catgtgagcc
tggaaagcat tgtgttgttt gcaccttttgt gaagttttta
aaaatgaaga tgcaagtgct tcattttcat ttctaaacac
```

```
taactccttt tatagactga taaaattttt ttctgaatat
ttcatgtgca tctttaacta aagggaatta atgtagagca
ggtactcctt aaagaacact aatttcatta tatactactc
gttgtacagc agcattcccg ttttcacagt gcctatttaa
aatgagagtt gaagtaaatg acatgctggt tgatttttat
caatattctg gacttaacgc atacctttca tgtctaagtc
atggttggct tttaaaactt tttataaagc ctcttgacaa
tgtacattgc taacaggtaa ctataggctt tgaaagtaat
gctcgtagat tcagtgttca cagtatgtgg cctccagcat
gtaacatgag gaatccttta tttcattaat taatggcttt
ttgacttgag ccaaaacata tgtaaaggaa acagaagtac
cgcacctcct cttacaccag tcagctcctt tgccttcagt
gttactagaa agcggcctgt gtccatgagt gtgctttgct
gttggtgcac tgaaaggcag gaaggagaca agattttcta
tttactcatc tcatgatgtc atttgaaggg catgtccaga
tatcttaaaa ttataatagg ctcaagaatc agtctcaggt
cacttacccc aaaaacattt gaaaatctga accacaatct
cctgaaagtt tttctcctat agattgttga caacacattg
ttttctggag gcatttgtgc cattaggttt ccattatcct
tcagtttttt tctttggtgt ttgggatgtc ttattttgtt
gccttatgtc cttttcaattttaaaatgttt gagtttgtat
atagttttga aattggatta tgtgttcatt gttgtttagt
ttgcattttt gtcaaattat ggttttgaag gttcatttgg
aacttactgt tagtctgtaa cagggttgcc cttgtccagt
atttatttat aagctgttta cttttcaagt tgataaaaac
attctccaat tctaaatttg cttgtgtcca taggtgatct
cttttagcaaa ctgagaaaaa aaggaagcta cttttaacat
gcaaagttcc ctcaaggtgt accgtgttgt ctctgtgggc
actcttcccc agcactttag cagtaattcc cccagctaca
cgctgcagtt gtactctgcc cactctagtg ttcctcagct
ctgctgtcct tttacttgta gctggatctt tgattatcct
tcgatttcca tgaaatatta atattgttgc cagcatagca
ggtacagtgg aagtcttgt cagtgagat tgtatcataa
tttaggattt aaaatgaatt aaagtttata
taaactgaagagtctccata tgtcaaactc ttggaaaatc
aaagatgttc caatttccta aacactagag aatacgagag
aaggtagagt ggaaaaggtt aggtaacctt gcaaaatatt
ttactatttt ctctaaatat gaggaagttt gagattatga
tctggatcta ccagatataa ctaaggttaa tttagcatga
aaaagtttta gtcatattgg catccaacct attcagtaac
cgaatcatag gacaatgatg gattaggaga acaatagagt
```

-continued

```
gggatcatta taaagaaaat aaattattaaaggtgtcttt
atcgttttag tgccattttt agtgtcttta ctataaatca
atatcagtgtattttatcat tctatgtgca tagcagaatt
ttcttttctc cctttttgttc ccctgtgaac ttggtgctta
ttaaagtgct cactgttctc ttaaaagaga gcagtggtat
aggtgtgcag tttccatgat gcaggttcca tttttaatat
attgttccac ttatcctttc ttctgagtaa attgctaatt
gtgccaaatt tatgtaatag ttttttgtaat gtggaataag
aattatgatg gaaccattgc acatttttt ctgaaacagc
cagtcaaggc agaacattaa tctccaaatg caagggctga
tctatttatt cattttggag gttgggtact ttattctttc
tttccgtcat ccttttcatt gtttcccccg gattctaatt
agttttttatt ttttttagat aactccaata taatcattac
agtttatgct ttaaatacta tgtgctttaa aaaggaaaat
gggaccaatt tgtctgctaa gaatttgatt ttaggtacta
taagagtatt aggaaaatat atacaactgg tgttaatttc
tagatatttt ctagaaatca cttgtgttcc tatttaataa
aaggtaattt agaatactac ttgtcctttg cagtagttta
gtaatgggca ttaagctgtg tcctcgaagg atgtacctat
tactaggtgc attttagaat gaaatattga tattttatta
gcatataatt gtggccatat atctcagatt ttctgaggca
gatctaattt tagataattc tgttggtaga ccatgtgatc
cttcttttttg gttttggaaa tataatcatt gttaatgttt
tccctccaaa tagaatactg ttttatccat acaaatcata
acagcatcta tcccatgcta gggttggaaa ctgatattgg
tattacttgt gtttttttctt agtgtgtttt atttcccagt
ttcatcttct tctaaaaatg aaaatatggt gccttccctc
cctccaggaa gactggcaaa tatttccttt tatttactgc
tgctgtggag tgatgagata tgcacttttac tctttaagat
tcagcaaaaa gcttttcact tctcagtata tccagaatac
atcatatctg ggacttagga aaatttgcca agcaatcttt
gttttttatag atactaatgt tgaccctctc cagcgttcaa
tgttataaat agaacaagtc aagctagtgt ttatctcctc
cccctccca aaactgtggc acagcatat aaaatgtacc
tcaataatgt tctattaaaa atgggacagg ggccttatgt
tttcataatt tcccaacaat gtgccgccat attttttgcct
caaggtaaag gttttaacag atgaaaagt acttcccaat
tccccgtgc tattcctaac ctataatgcc caaatgtttt
gtgcaatgtg tagtgtgtgt gtataaatac atatattctt
gaaatagaca taccatcaga gacatcattc acaagtaact
gatgtattgg catctcattc atatttctga tgtgtgaggt
atatggtact aattaccttt tccttgatgt ttgccaaatt
tgaataaagg cattggtacg aaattacaga atgtaaagaa
aatgttttg gcttgaaaaa ttaacatatt ttatgacgta
ccacagtata ctctgcccaa accagcaccc tatctatctt
tcctgttctt tacatccctg ttccccatcc ctacttcctc
attttttggta taacacagtt cttttgtagc atcattataa
ttgcagttct atggcaattg gacagttata gcatggaaac
agactggtat aagtagtaca gtagtcacca gtgtgccaca
tttgcattag taatgcaaaa tatacatttt ataaaggaca
aactttgtgt tatgttttat tttcattaca ttgtataata
ttgtaagact attgtatgtc ctaatttgca ttataaatgt
tttttttccta cgtaaaggca taaatatagc aactttgtat
aaaggtagct tattagattt ttaattttttt cttttataaa
aaattgtcca acagtgggac taccattgcc aaattgtata
tgaaatatga atttttacccc catggttaat ttcttttata
aacattccat atttctctaa taaaaagaca taagtgatac
tgtactatgc atacattgta tcttaatgct gtttcagatc
agcattttaa attttggttt gcatttttaa tattggcaaa
acgtaaccac tgttaattaa aataaaaccct tgttgtatat
gtaacaacat aattttccct ctatcccttc ccaccctttg
ttctctattt ctccctatca gtgccaactt catacatttt
gtagcatggc aataaaaatat aacttttaca ctgaggccga
gtgtggcttt ttggaggaag tggggatggg acgattgccc
tctagttgtc ctttgcatat gactgttttt tgccatataa
gccatgtcat caggcatgaa aagttttctc atatatgatg
taaacttgct tttaaggaca agtgtgaatg tgcttttttaa
gcttaatttt tgtcatgaca actaatttttt tttatctttg
gagaagtcag agttctttac aatcaaacgt ttattaactg
gagtacttag aataagctag taattgaatt tagttcaagg
gctaagcaac acatttttaa atccttattt attgtagagt
attagtatac tgtcctacaa attatgtaaa atatggttta
atattagatg actttggatt ttgcaatgcc ttactgttgt
cattctagca taaatatcca taatgaggta ctcaagttga
tactggaagctgagctgatc atacactgac ctgaagcatt
catgaaaagc tgctttattg aataaagtct gattggagtt
cttttcatgc tcactttccc cttattgctg aaagtagatt
gcaataaaacccaataaaa cgtttggtcg gataaaaaaa
aaaaaaaaa aa
```

SEQ ID NO: 8 ANXA1 (NP_000691.1) mamvseflkq awfieneeqe yvvqtvksskg gpgsayspyp tfnpssdvaa lhkaimvk-gvdeatiidilt krnnaqrqqi kaaylqetgk pldetlkkal tghleevvla llktpaqfda delraamkgl gtdedtliei lasrtnkeir dinrvyreel krdlakdits dtsgdfrnal lslakgdrse dfgvnedlad sdaralyeag errkgtdvnv fntilttrsy pqlrrvfqky tkyskhdmnk vldlelkgdi ekcltaivkc atskpaffae klhqamkgvg trhkalirim vsrseidmnd ikafyqkmyg islcqailde tkgdyekilv alcggn SEQ ID NO: 9 Hp2 (NP_001119574.1) msalgavial llwgqlfavd sgndvtdiad dgcpkppeia hgyvehsvry qcknyyklrt egdgvytlnn ekqwinkavg dklpeceavc gkpknpanpv qrilgghlda kgsfpwqakm vshhnittga tlineqwllt taknlflnhs enatakdiap tltlyvgkkq lveiekvvlh pnysqvdigl iklkqkvsvn ervmpiclps kdyaevgrvg yvsgwgrnan fkftdhlkyv mlpvadqdqc irhyegstvp ekktpkspvg vqpilnehtf cagmskyqed tcygdagsaf avhdleedtw yatgilsfdk scavaeygvy vkvtsiqdwv qktiaen SEQ ID NO: 10 Zinc alpha2-glycoprotein (Chain B, Crystal structure of the complex formed between Mhc-Like Zinc Alpha2-glycoprotein and Prol) qdntrkiiik nfdipksvrp ndevtavlav qtelkecmvv ktylissipl qgafnykyt cicddnpktf ywdfytnrtv qiaavvdvir elgicpddaa vipiknnrfy tieilkve SEQ ID NO: 11 (calprotectin) mltelekaln siidvyhkys likgnflhavy rddlkkllet ecpqyirkkg advwfkeldi ntdgavnfqe flilvikmgv aahkkshees hke All references, publications, patent applications, issued patents, accession records and databases cited herein, including in any appendices, are incorporated by reference in their entirety for all purposes.

We claim:

1. A method for diagnosing the presence of lung cancer in a subject at risk of having lung cancer, the method comprising: a) contacting a saliva sample from the subject with a set of at least three reagents, wherein the set of at least three reagents specifically binds to at least three biomarkers in the saliva sample, wherein the three biomarkers are selected from the group consisting of BRAF, EGFR, FGF19, LZTS1, CCNI, GREB1, and FRS2; b) measuring the level of the at least three biomarkers in the saliva sample; c) detecting that the level of the at least three biomarkers is increased in the saliva sample relative to a control sample from a subject without lung cancer, thereby detecting the presence of lung cancer in the subject; and d) administering a lung cancer therapy to the subject, wherein the lung cancer therapy is selected from the group consisting of chemotherapy, hormonal therapy, radiotherapy, immunotherapy, and surgical removal of lung tissue.

2. The method of claim 1, wherein the assay detects at least three nucleic acids encoding at least three biomarkers, and wherein the at least three nucleic acids are detected by mass spectroscopy, PCR, microarray hybridization, thermal sequencing, capillary array sequencing, or solid phase sequencing.

3. The method of claim 1, wherein the assay that specifically detects at least three biomarkers in the saliva sample, detects at least four biomarkers selected from the group consisting of BRAF, EGFR, FGF19, LZTS1, CCNI, GREB1, and FRS2.

4. The method of claim 1, wherein the assay that specifically detects at least three biomarkers in the saliva sample, detects at least five biomarkers selected from the group consisting of BRAF, EGFR, FGF19, LZTS1, CCNI, GREB1, and FRS2.

* * * * *

SEQUENCE LISTING

```
<160> NUMBER OF SEQ ID NOS: 11

<210> SEQ ID NO 1
<211> LENGTH: 2811
<212> TYPE: DNA
<213> ORGANISM: Homo sapiens

<400> SEQUENCE: 1
ccatttcaat agtcgcggga tacttgaact gcaagaacag ccgccgctcc ggcgggctgc     60
tcgctgcatc tctgggcgtc tttggctcgc cacgctgggc agtgcctgcc tgcgcctttc    120
gcaacctcct cggccctgcg tggtctcgag ctgggtgagc gagcgggcgg gctggtaggc    180
tggcctgggc tgcgaccggc ggctacgact attctttggc cgggtcggtg cgagtggtcg    240
gctgggcaga gtgcacgctg cttggcgccg caggctgatc ccgccgtcca ctcccgggag    300
cagtgatgtt gggcaactct gcgccggggc ctgcgacccg cgaggcgggc tcggcgctgc    360
tagcattgca gcagacggcg ctccaagagg accaggagaa tatcaacccg gaaaaggcag    420
cgcccgtcca acaaccgcgg acccgggccg cgctggcggt actgaagtcc gggaacccgc    480
ggggtctagc gcagcagcag aggccgaaga cgagacgggt tgcacccctt aaggatcttc    540
ctgtaaatga tgagcatgtc accgttcctc cttggaaagc aaacagtaaa cagcctgcgt    600
tcaccattca tgtggatgaa gcagaaaaag aagctcagaa gaagccagct gaatctcaaa    660
aaatagagcg tgaagatgcc ctggctttta attcagccat tagtttacct ggacccagaa    720
aaccattggt ccctcttgat tatccaatgg atggtagttt tgagtcacca catactatgg    780
acatgtcaat tgtattagaa gatgaaaagc cagtgagtgt taatgaagta ccagactacc    840
atgaggatat tcacacatac cttagggaaa tggaggttaa atgtaaacct aaagtgggtt    900
acatgaagaa acagccagac atcactaaca gtatgagagc tatcctcgtg gactggttag    960
ttgaagtagg agaagaatat aaactacaga atgagaccct gcatttggct gtgaactaca   1020
ttgataggtt cctgtcttcc atgtcagtgc tgagaggaaa acttcagctt gtgggcactg   1080
ctgctatgct gttagcctca aagtttgaag aaatataccc cccagaagta gcagagtttg   1140
tgtacattac agatgatacc tacaccaaga aacaagttct gagaatggag catctagttt   1200
tgaaagtcct tacttttgac ttagctgctc caacagtaaa tcagtttctt acccaatact   1260
ttctgcatca gcagcctgca aactgcaaag ttgaaagttt agcaatgttt ttgggagaat   1320
taagtttgat agatgctgac ccatacctca agtatttgcc atcagttatt gctggagctg   1380
cctttcattt agcactctac acagtcacgg gacaaagctg gcctgaatca ttaatacgaa   1440
agactggata taccctggaa agtcttaagc cttgtctcat ggaccttcac cagacctacc   1500
tcaaagcacc acagcatgca caacagtcaa taagagaaaa gtacaaaaat tcaaagtatc   1560
```

| | |
|---|---|
| atggtgtttc tctcctcaac ccaccagaga cactaaatct gtaacaatga aagactgcct | 1620 |
| ttgttttcta agatgtaaat cactcaaagt atatggtgta cagttttaa cttaggtttt | 1680 |
| aattttacaa tcatttctga atacagaagt tgtggccaag tacaaattat ggtatctatt | 1740 |
| acttttaaa tggttttaat ttgtatatct tttgtatatg tatctgtctt agatatttgg | 1800 |
| ctaattttaa gtggttttgt taaagtatta atgatgccag ctgtcaggat aataaattga | 1860 |
| tttgaaaaac tttgcaagtc aaatttaact tcttcaggat tttgcttagt aaagaagttt | 1920 |
| acttggttta ctatataatg ggaagtgaaa agccttcctc taaaattaaa gtaggtttag | 1980 |
| gaaaacagac cctcaaattc tgacattcat tttcctaagc aactggatca atttgctgac | 2040 |
| ttgggcataa tctaatctaa gcatatctga atacagtatt cagagataga tacagtagag | 2100 |
| attccccaga cttttcgct ctttgtaaaa cctgtttgtt taggttttgc gaggtaaact | 2160 |
| caacagaggt tgggagtgga agagggtggg aagcttatat gcaaattaac agacgagaaa | 2220 |
| tgctccagaa ggtttattat tttaaagcac attaaaaaca aaaaactatt tttaaaatcc | 2280 |
| tgctagattt tataatggat ttgtgaataa aaaatacca gggttctcag aatgaataa | 2340 |
| atatcccttt taatagttat atatacagat atacaactgt tagctttaat tggcagctct | 2400 |
| cttctttttt cttcttttca ctggcttttt acttggtgct ttttcttgtt ttgcactggt | 2460 |
| ggtctgtgtt ctgtgaataa agcaaagtaa gaatttacta agagtatgtt aagttttgga | 2520 |
| ttattgaaat aagaggcatt tcttagtttt ccagtaggat ctaaaatgtg tcagctatga | 2580 |
| gtaagactgg catccaagaa gtttatatta tagatttagg tcctaatttt tataaatcac | 2640 |
| aaggtaaaaa aatcacagaa cagatggatc tctaatgaaa aagggatgtc tttttgttta | 2700 |
| tagtcatgtg gcaagatgag agtaaaacca gagagcaaac ctctataagt gttgagtata | 2760 |
| tgtatacatt tgaaataaac cagaaatttg ttaccttaaa aaaaaaaaaa a | 2811 |

<210> SEQ ID NO 2
<211> LENGTH: 5616
<212> TYPE: DNA
<213> ORGANISM: Homo sapiens

<400> SEQUENCE: 2

| | |
|---|---|
| ccccggcgca gcgcggccgc agcagcctcc gccccccgca cggtgtgagc gcccgacgcg | 60 |
| gccgaggcgg ccggagtccc gagctagccc cggcggccgc cgccgcccag accgacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcacttttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caaccctgc cctgtgcaac | 720 |
| gtggagagca tccagtggcg ggacatagtc agcagtgact ttctcagcaa catgtcgatg | 780 |
| gacttccaga accacctggg cagctgccaa agtgtgatc caagctgtcc aatgggagc | 840 |
| tgctggggtg caggagagga gaactgccag aaactgacca aaatcatctg tgcccagcag | 900 |

```
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcaggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg   2160
aatgggccta agatcccgtc catcgccact gggatggtgg ggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caagacaat attggctccc agtacctgct caactggtgt   2700
gtgcagatca aagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg accttggat ccaagccata tgacggaatc   3000
cctgccagcg agatcctctc catcctggag aaaggagaac gctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc aggggggatga agaatgcat ttgccaagtc ctacagactc caacttctac   3240
```

```
cgtgccctga tggatgaaga agacatggac gacgtggtgg atgccgacga gtacctcatc      3300
ccacagcagg gcttcttcag cagcccctcc acgtcacgga ctcccctcct gagctctctg      3360
agtgcaacca gcaacaattc caccgtggct tgcattgata gaaatgggct gcaaagctgt      3420
cccatcaagg aagacagctt cttgcagcga tacagctcag accccacagg cgccttgact      3480
gaggacagca tagacgacac cttcctccca gtgcctgaat acataaacca gtccgttccc      3540
aaaaggcccg ctggctctgt gcagaatcct gtctatcaca atcagcctct gaaccccgcg      3600
cccagcagag acccacacta ccaggacccc cacagcactg cagtgggcaa cccgagtat      3660
ctcaacactg tccagcccac ctgtgtcaac agcacattcg acagccctgc ccactgggcc      3720
cagaaaggca gccaccaaat tagcctggac aaccctgact accagcagga cttctttccc      3780
aaggaagcca agccaaatgg catctttaag ggctccacag ctgaaaatgc agaataccta      3840
agggtcgcgc cacaaagcag tgaatttatt ggagcatgac cacggaggat agtatgagcc      3900
ctaaaaatcc agactctttc gatacccagg accaagccac agcaggtcct ccatcccaac      3960
agccatgccc gcattagctc ttagacccac agactggttt tgcaacgttt acaccgacta      4020
gccaggaagt acttccacct cgggcacatt ttgggaagtt gcattccttt gtcttcaaac      4080
tgtgaagcat ttacagaaac gcatccagca agaatattgt ccctttgagc agaaatttat      4140
ctttcaaaga ggtatatttg aaaaaaaaaa aaagtatatg tgaggatttt tattgattgg      4200
ggatcttgga gtttttcatt gtcgctattg atttttactt caatgggctc ttccaacaag      4260
gaagaagctt gctggtagca cttgctaccc tgagttcatc caggcccaac tgtgagcaag      4320
gagcacaagc cacaagtctt ccagaggatg cttgattcca gtggttctgc ttcaaggctt      4380
ccactgcaaa acactaaaga tccaagaagg ccttcatggc cccagcaggc cggatcggta      4440
ctgtatcaag tcatggcagg tacagtagga taagccactc tgtcccttcc tgggcaaaga      4500
agaaacggag gggatggaat tcttccttag acttactttt gtaaaaatgt ccccacggta      4560
cttactcccc actgatggac cagtggtttc cagtcatgag cgttagactg acttgtttgt      4620
cttccattcc attgttttga aactcagtat gctgcccctg tcttgctgtc atgaaatcag      4680
caagagagga tgacacatca ataataact cggattccag cccacattgg attcatcagc       4740
atttggacca atagcccaca gctgagaatg tggaatacct aaggatagca ccgcttttgt      4800
tctcgcaaaa acgtatctcc taatttgagg ctcagatgaa atgcatcagg tcctttgggg      4860
catagatcag aagactacaa aaatgaagct gctctgaaat ctcctttagc catcacccca      4920
acccccaaa attagtttgt gttacttatg aagatagtt ttctcctttt acttcacttc        4980
aaaagctttt tactcaaaga gtatatgttc cctccaggtc agctgccccc aaaccccctc      5040
cttacgcttt gtcacacaaa aagtgtctct gccttgagtc atctattcaa gcacttacag      5100
ctctggccac aacagggcat tttacaggtg cgaatgacag tagcattatg agtagtgtgg      5160
aattcaggta gtaaatatga aactagggtt tgaaattgat aatgctttca caacatttgc      5220
agatgtttta gaaggaaaaa agttccttcc taaaataatt tctctacaat tggaagattg      5280
gaagattcag ctagttagga gcccacccttt tttcctaatc tgtgtgtgcc ctgtaacctg     5340
actggttaac agcagtcctt tgtaaacagt gtttttaaact ctcctagtca atatccaccc    5400
catccaattt atcaaggaag aaatggttca gaaatatttt tcagcctaca gttatgttca     5460
gtcacacaca catacaaaat gttccttttg cttttaaagt aattttttgac tcccagatca    5520
gtcagagccc ctacagcatt gttaagaaag tatttgattt ttgtctcaat gaaaataaaa      5580
ctatattcat ttccactcta aaaaaaaaaa aaaaaa                                5616
```

<210> SEQ ID NO 3
<211> LENGTH: 4544
<212> TYPE: DNA
<213> ORGANISM: Homo sapiens

<400> SEQUENCE: 3

```
actctgcgcg ccggcggggg ctgcgcagga ggagcgctcc gcccggctac aacgctccgc      60
gagccggcgc ggcaacacct gttcgcggca gcctgggcgg cacgcgagct cccggacgcg     120
gctctcctcg ctcgccgctc gccacccgtt ctaagccaat ggacatctgc cgagcctctg     180
gagaatcctg gatactagct ttggacgcct aaagtttctt cttcttttg ttttattatt      240
attatcattt tttggagggg ggaccgggag gggagatttg tcgccgccac caacgtgaga     300
ttttttttc cccttgaagg attcatgctg atgtctgcag agtcggttag agagtaaaaa      360
cagcgcatgc cttcctggag tcaggatccg taaattctga cgtagcccgt gcatcttaaa     420
aatccctata ataacgccta ggcatttaag ttgctatggt cattctgatc tcaaaccaaa     480
tggagaaact acggattttt tttccttatt acggtcggat gggatgaaga ccttcctgcc     540
tgctaagagc tggggatcta tctatagaga tacatagata tgtttatcaa tatgtcagtg     600
tgtgagtata aagtggtggt ttcttagact atcagtggtt tgaccttgaa cctgtgccag     660
tgaaacagca gattactttt atttatgcat ttaatggatt gaagaaaaga accttttttt     720
tctctctctc tctgcaactg cagtaaggga ggggagttgg atatacctcg cctaatatct     780
cctgggttga caccatcatt attgtttatt cttgtgctcc aaaagccgag tcctctgatg     840
gctcccttag gtgaagttgg gaactatttc ggtgtgcagg atgcggtacc gtttgggaat     900
gtgcccgtgt tgccggtgga cagcccggtt ttgttaagtg accacctggg tcagtccgaa     960
gcaggggggc tccccagggg accgcagtc acggacttgg atcatttaaa ggggattctc    1020
aggcggaggc agctatactg caggactgga tttcacttag aaatcttccc caatggtact    1080
atccagggaa ccaggaaaga ccacagccga tttggcattc tggaatttat cagtatagca    1140
gtgggcctgg tcagcattcg aggcgtggac agtggactct acctcgggat gaatgagaag    1200
ggggagctgt atggatcaga aaaactaacc caagagtgtg tattcagaga acagttcgaa    1260
gaaaactggt ataatacgta ctcatcaaac ctatataagc acgtggacac tggaaggcga    1320
tactatgttg cattaaataa agatgggacc ccgagagaag ggactaggac taaacggcac    1380
cagaaattca cacatttttt acctagacca gtggaccccg acaaagtacc tgaactgtat    1440
aaggatattc taagccaaag ttgacaaaga cagtttcttc acttgagccc ttaaaaaagt    1500
aaccactata aaggtttcac gcggtgggtt cttattgatt cgctgtgtca tcacatcagc    1560
tccactgttg ccaaactttg tcgcatgcat aatgtatgat ggaggcttgg atgggaatat    1620
gctgattttg ttctgcactt aaaggcttct cctcctggag ggctgcctag ggccacttgc    1680
ttgatttatc atgagagaag aggagagaga gagagactga cgctaggag tgtgtgtatg     1740
tgtgtgtgtg tgtgtgtgtg tgtgtgtgta tgtgtgtagc gggagatgtg ggcggagcga    1800
gagcaaaagg actgcggcct gatgcatgct ggaaaaagac acgcttttca tttctgatca    1860
gttgtacttc atcctatatc agcacagctg ccatacttcg acttatcagg attctggctg    1920
gtggcctgcg cgagggtgca gtcttactta aaagactttc agttaattct cactggtatc    1980
atcgcagtga acttaaagca aagacctctt agtaaaaaat aaaaaaaat aaaaataaa      2040
aataaaaaaa gttaaattta tttatagaaa ttccaaaggc aacattttat ttattttata    2100
```

```
tatttattta ttatatagag tttattttta atgaaacatg tacaggccag ataggcattt    2160
tggaagcttt aggctctgta agcattaaat ggcaaagtcc gctatgaacc tgtggtaaat    2220
tcatgcaagt agatataatg gtgcatggat ataagaaatt ctaatgaccc taatgtacta    2280
aaggcgacaa tctcttttgt gcccatatta ttgtaaactt atgcacatcg ctcatgacac    2340
tgagtattca ctcttcagac tgcttgtttc atagcttatc ccagaggatt aaagataaac    2400
tgggtctcaa actttgattc tgtgtctgca atatttcctc tctcataagt gactccacta    2460
ttgtaacttc atggttggaa aatatgaggg ttgatatatg tcttacttgt ttaaatctgt    2520
cgcagaatat accaaagcta ataataact atgctttcat tttagccgat ctccagaatg     2580
acagtattaa catcaaacat tgtattgatt tagaattctc aaaaaaggaa aaaaagtac     2640 atagcacaga ctatttttt taaagacgta agaatcagat taacaggatc atacttgtaa     2700 acttttttg gttcacttgg ctatcaaata tgaaattata gaagtatcat aggggtcatt     2760
gtaacatctt ttagagaaaa tggctatcag tgtgaactgt cataattacg tggtaataga    2820
cccttagtaa aacttgcaaa atgaaactaa taaatcgtta tcaataatga caatgagggg    2880
gaaagtatta tacttgttga ctgtgttttg ttttttaaaa tggtctccac aagcgctcaa    2940
tttttttaga ggggatatta ctatatagaa tatcttttac aaggctttta taacattta     3000 tgctgaaaag cataagaata cgtatttctt tagtagcaat aattttggaa cttgcccttg    3060
ggcaagcgag actatttctt actatatact aaggagaaaa gagccaaatt cttaaagcaa    3120
tatttaagaa aaaaggaatt tataacaaat tctcatctac atatgacact ttctagccag    3180
ttgtgttgag aagtgcaaag tgacggttta aacatgtgtt gggatttatt gaactaattt    3240
taaaatttac tattcaaact ttattttgct ctgatgcaca ttctctatga aaaataaaag    3300
tgtgtcactg gtgagtgaca gctgttatga gctagaagcg catgacttat tgtgacgatg    3360
tcttgccttt ctgtggtcca agttggagta catggcaatg ccctcctgct gatgtgcatt    3420
aaggaaaatc taagtctaat atttggaatt aagatatatt ttaggggggag gggacagaag    3480 caatgtaaaa tagttgattt atgataaagc tcagaatgtc ctcttcattt attttcttgt    3540
tttattttcc tttctaaaca gaaactgcat ttaattccaa aaagtagtat tcttatttat    3600
tatttaaccc tttgctgctg ctaaaatgtg cacatattca ggctttagtt tttccaaaag    3660
gcattttttt tttggctgaa aaatattaaa catttgacca cagggaagaa tcaagtttct    3720
aggatgtcat aggtatacta tgtagcactg aaaaaattga ttttaggtga cagccaaaag    3780
tagtcttaaa gtagcatgag accttagata atcgacctaa aagaaagaaa attgtgaaaa    3840
agacaaaaat cttcatgcat tcctataaaa cgctacttta aggtctactt ttggagttaa    3900
ttttgtttgg tactttttt tttttttaaga cgagcaaatt gttatatgct tttggcaatt    3960
gatacaataa actgtaatgg tctgtaaata aataaatatt gactcatgcg atttatgtaa    4020
atagtggaac tgggagagtg gatggctcag ggtttcggtg tgggcattgt ctcttgggca    4080
gtagagtgag tcatccccag ctcatgggtt tgcatccagt tcttgtctta agagacccaa    4140
agcccagtga atggcagccc tgagccactg tggaatgggg gttctggttt cacaaacaga    4200
tgcttagata gccaaaccac tgtccttgttg gtgccaacac ttgcactgtg gtcaaagact    4260
taccgagcat gggctgaaca accttcccat ctgtcatgtg aatgtcccca agcagtggtg    4320
aaggacatgc taggtcagtg ttggggaacc tgccctgcca ggtcctgttt tgtagataaa    4380
caaatggctg ccttctggtg ttttttattct atttcatctc attaacacta caaccttgtg    4440
ttatttactt gataatctgt aattgtatgt aaatacatac aggattatgt aatttgtgta    4500
```

```
                                                           -continued aatacataat tacagagttt tgaaaactga aaaaaaaaaa aaaa             4544

<210> SEQ ID NO 4
<211> LENGTH: 2346
<212> TYPE: DNA
<213> ORGANISM: Homo sapiens

<400> SEQUENCE: 4
gaaagaatca aagcgcacat cttgtacttt gatgcccata ggaagggctc tcctctggcc   60
cctctggctt tgtttggagc agaaaacaac aaactgcagc tgaggacagc cacccttttct  120 tcgtctctgc tgagcgaagg ctacacggcc cttcctcctt gcagctgttt caccttctac  180
cttgcgtgga gccaggcttt tgcaccgaat ctgagatgcc attttaaaca gaagactcca  240
tcctcttgaa gatgggaaat tcttacgctg acagctgaa gacgacacgc tttgaagagg   300
tcttgcacaa ttccatcgag gcatccctgc ggtccaacaa cctggtgccc aggcccatct  360
tttcccagct gtacctggaa gctgagcagc agcttgccgc tctagaaggt ggtagccgag  420
tggacaatga ggaagaggaa gaagagggag aaggagggct ggaaacaaat ggccccccaa  480
accctttcca gctgcaccct ctgcctgaag gatgctgtac cacagacggg ttttgccagg  540
ccgggaagga cctgcgcctt gtctccattt ccaacgagcc catggatgtc cctgcgggct  600
ttctcctcgt gggggtcaag tcccccagcc tgccggacca tctcctggtg tgcgccgttg  660
acaagaggtt cttgccagat gacaatggcc acaatgctct tcttggtttc tctgggaatt  720
gtgttggctg tggaaagaaa ggcttctgtt acttcacgga attctccaat catataaatc  780
tgaaactgac cactcaaccc aagaagcaga acacttgaa gtattacctg gtccgtaatg   840
cacaagggac tctaaccaaa ggacctttaa tctgttggaa aggctcagag tttagaagcc  900
ggcagatccc cgccagtact tgttccagtt ccctcttccc agccctggag agcacggctc  960
cttccccagc gagcccgttc ctgggacgaa ccccagcatc ctgatgggag ctcagcaggc 1020
aggaccagct tctgatcacc cctcactaaa cgcagcaatg ggtccggctg ttttcaacgg  1080
caaagattcc ccgaagtgcc aacaactggc aaagaataac ctgttggccc tgccgcgacc  1140
atcggcttta ggtatcttgt caaactccgg gcccccaaa aaacgccaca aagggtggtc   1200
tccagaatct ccatcagctc cagatggtgg ctgcccccaa ggtggtggga acagagctaa  1260
gtatgagagc gcaggcatgt cctgcgtgcc gcaggttggc ttggtgggac cagcttcagt  1320
cacctttcca gtggtggcct ctggagaacc agtgtctgtt cctgacaact tgctgaaaat  1380
atgcaaggcc aagccagtga tatttaaagg ccatgggaac ttcccttacc tctgtgggaa  1440
cctgaatgac gtcgtggtca gcccccctctt gtacacgtgc taccagaatt cccagtctgt  1500
ctcacgggca tacgagcagt acggcgcctc tgccatccag cccatctccg aggagatgca  1560
gctcctgctt accgtctact acctggtcca gctggcacat caaatacgaa atccggacgt  1620
ataaaccaga caattcataa aagagaaaat accagaagga aacaaatatt gaaaagtatt  1680
cagtctcact catcatcaaa gacatgcaaa tcacaaatca agtcatcttt ttctgaatta  1740
ataacccaaa tgatggtacc cagtggtgct taggtgcggt aaaaccagcg cttgtccgat  1800
gcaccgttcg cgtggtaaac tgacgcattc aggctcttgg gaagcaatct gatgatatgt  1860
agtagctggt tctgtaaatc cacctttgag aatttaggcg aaggaagtaa cgttctatat  1920
gtcaagatgt gcattgcaga gggatttata aaggtgaata tttggaagaa ataagagaat  1980
ccacaataga gaccttgcta agtaaacggt ggtgctcacg tatgatggga cattatggac  2040
```

| | |
|---|---|
| acactaacag cactctttat gttggctgaa aatggcactg aaactgatga tagggtcatg | 2100 |
| gttaaggaaa gaatgcaaga cccaaagttt atactgacaa tcattgcagc tatttgtaag | 2160 |
| gacagtttta atactaattc cagcaataca tgtttttatt ccctgtcctg gagtaggaga | 2220 |
| aagcctatat tcccaggctg aatgttctac acatttacca ctgtatatgc acatagggac | 2280 |
| agtgtaacct gtctatacca ccgtagttcc agtcctaact ttctgaattc tgtttaaaga | 2340 |
| ccttct | 2346 |

<210> SEQ ID NO 5
<211> LENGTH: 5456
<212> TYPE: DNA
<213> ORGANISM: Homo sapiens

<400> SEQUENCE: 5

| | |
|---|---|
| tgagggcttt gctatgacct cagtcccctc acggagccac gactgcccct tgctgccaca | 60 |
| gcctttccaa gaccctgccc ggccctgccc catcctcagc cccgagtcac catgggcagc | 120 |
| gtcagtagcc tcatctccgg ccacagcttc cacagcaaga ctgccgggc ttcgcagtac | 180 |
| aagctgcgca gtcctcccca cctcaagaag ctcaaccggt attccgacgg gctgctgagg | 240 |
| tttggcttct cccaggactc cggtcacggc aagtccagct ccaaaatggg caagagcgaa | 300 |
| gacttcttct acatcaaggt cagccagaaa gcccggggct cccatcaccc agattacacg | 360 |
| gcactgtcca gcggggattt aggggccag gctggggtgg acttttgaccc gtccacaccc | 420 |
| cccaagctca tgcccttctc caatcagcta gaaatgggct ccgagaaggg tgcagtgagg | 480 |
| cccacagcct tcaagcctgt gctgccacgg tcaggagcca tcctgcactc ctcccccggag | 540 |
| agtgccagcc accagctgca ccccgcccct ccagacaagc caaggagca ggagctgaag | 600 |
| cctggcctgt gctctgggc gctgtcagac tccggccgga actccatgtc cagcctgccc | 660 |
| acacacagca ccagcagcag ctaccagctg gacccgctgg tcacacccgt gggacccaca | 720 |
| agccgttttg ggggctccgc ccacaacatc cccagggca tcgtcctcca ggacagcaac | 780 |
| atgatgagcc tgaaggctct gtccttctcc gacggaggta gcaagctggg ccactcgaac | 840 |
| aaggcagaca agggcccctc gtgtgtccgc tcccccatct ccacggacga gtgcagcatc | 900 |
| caggagctgg agcagaagct gttggagagg gagggcgccc tccagaagct gcagcgcagc | 960 |
| tttgaggaga aggagcttgc ctccagcctg cctacgagg agcggccgcg cgctgcagg | 1020 |
| gacgagctgg agggccgga gcccaaaggc ggcaacaagc tcaagcaggc ctcgcagaag | 1080 |
| agccagcgcg cgcagcaggt cctgcacctg caggtactgc agcttcagca ggagaagcgg | 1140 |
| cagctccggc aggagctcga gagcctcatg aaggagcagg acctgctgga gaccaagctc | 1200 |
| aggtcctacg agagggagaa gaccagcttc ggccccgcgc tggaggagac ccagtgggag | 1260 |
| gtgtgccaga gtcaggcga gatctccctc ctgaagcagc agctgaagga gtcccagacg | 1320 |
| gaggtgaacg ccaaggctag cgagatcctg gtctcaagg cacagctgaa ggacacgcgg | 1380 |
| ggcaagctgg agggcctgga gctgaggacc caggacctgg agggcgccct gcgcaccaag | 1440 |
| ggcctggagc tggaggtctg tgagaatgag ctgcagcgca agaagaacga ggcggagctg | 1500 |
| ctgcgggaga aggtgaacct gctggagcag gagctgcagg agctgcgggc ccaggccgcc | 1560 |
| ctggccgcg acatggggcc gcccaccttc cccgaggacg tccctgccct gcagcgggac | 1620 |
| tggagcgggct gcgggccgag ctgcgggagg agcggcaagg ccatgaccag atgtcctcgg | 1680 |
| gcttccagca tgagcggctc gtgtggaagg aggagaagga gaaggtgatt cagtaccaga | 1740 |
| aacagctgca gcagagctac gtggccatgt accagcggaa ccagcgcctg gagaaggccc | 1800 |

-continued

```
tgcagcagct ggcacgtggg gacagcgccg gggagcccct ggaggttgac ctggaagggg    1860
ctgacatccc ctacgaggac atcatagcca ctgagatctg aggggctgcc tgggaaggcg    1920
agtctgggga cctggcactg ggaggcaggg ctctcccgtg catccccct gctcagcaat     1980 tcagacccct tgagagacg ccactccctg ggacacagac ccaggacccc cgaggggagg     2040
gcaggatggc ctttccttcc ctctctgatg tcccagtgct caccagccct gcagcccacc    2100
agacgtcagg ccctgactcc tctggctttc caggagatg gtccagggg tctgtctgct      2160 ttggttaagg gctccctaaa ctttggcctt tgttcgaaat agatatcctc tcccctcct     2220 ccagggaagg tggccacagc aagtacagcg ctcccctct gcttctcatc caacctctt      2280 tttcctcctg gacacattgg aatgccttgg aaatagaaag aagccatata tgaccagaag    2340
ccttggaacc agcccccatca gaacctgagc tattttcctc tggccgcaga ggtgtagggt   2400
ggaatgagcc gcgggaagc tggctttgaa acctcagggc tgtcccagcc ccggcaagcc     2460
acaggaagga ggggagagac aggcagccca gcagtgtgga gaccctgcca cagccagagg   2520
agggcagagg gagaatccaa gggttgagag ccagtggcgg gtgatggcca gccctgggg    2580 cccagcccct gtttactggt tcttgcaaat gggagctgag cagcctctgg acagccagtg    2640
acctttgacc tcggtgacca ctcttcttta agccatagac cctgaggccc tgggctgggt    2700
gctgggaagg gagggttgaa accaccgtga accagagggt gtggctttcc aggcaccctc    2760
agggagcctc cccatctgtc cagctggggc cagaggctgg gagtccctac ctgcttcacg    2820
ttggccggcg gctactctgg aatgttttc cctccccaga atcaagcttt tgcttgatcc      2880
agaagagccc atatcactaa gatggcatat atgtgatctg ggcattttcc tcctctgcct    2940
acagccaggt ttagcggcaa accttttcccc cttagcacct tcaggctga gttctgggtt    3000 tctagaggtc aggacggctc ctcagagcgc caggaagcca gagccccaag caggacgaaa    3060
aagaggcata cacacagcag tgtgaatagc ctggccacca gccatcctcc ctccacctca    3120
agacccccat ttgtcccaga ctaaaggatc cagagagcag ctccctttct caggagcttg    3180
ggcagtgccc cagggagtcc agggtttctc tgcagatgtg cggagcggga ggcggtggta    3240
gagagagata aaaggtggag tttctctgtt gtttggttca gggattttat ttttaatttt    3300
atgagacagg gtcttgctct gtcccccagg ctggagtgca gtggcatgat catagctcac    3360
tgcagcctca tactcctggg ctcaagcaat cctcctgcct cagccttcca actagctggg    3420
actacaggtg cgcgccaccg tgcctggcta acttttcatt tttttgtag ggacggggtc     3480 tcgttttgtt gccaaagctg gtctcaaact tgtggcctca gcaatccac ctgccttggc     3540 ctcccaaagt gctgagattg cagatgtgag ccaccgtgcc tggccagatt tttcttttat    3600
tcttctttct ttttctttt tgctttcttg tcttttcaga agcaagccag acctagcagg     3660
ctgttccatg ttctattttt gactgtagcc acagctgctg ttctcaggac agcatccctt    3720
cccacatgcc tgcgcctgct gcctgctgag atgaggaggg gagcgtctgg gaacttgcga    3780
gtccaaggcc agtccccatt tctgcctcgc tcaccgctgg cccttagaga ccccgaggta    3840
ggggtgggga gatgcttctc tccttgcccc ccgccctcat gggtcctagc ccttccctga    3900
gtgcgggctg aggccagagt cacctttct gtggctggct ctaccttcct gtccctgagg    3960
ttaaacggtg cccatcctgc catcctcaaa cgacagagga gcttttctgg aatttcaaac    4020
cattgctctt agtcccaagc taggcttaaa cctggaatct acaagccaaa agtccctccc    4080
tgcctgaggg cagtacccctc cattgggcac agtccagacc caagtcaaag atgccccatt   4140
```

-continued

```
ccttgcgcct cagccctcag ttccttcatt tccaccaggc cgtgccttgt ttgagttttt    4200
cctcccagtg agactgcccc acggagacag aggaaagggc tggctccccc tccccaggct    4260
ggagaccccc ccccaactcc aggaaagagc agtcagagtc cagtgctctg cctcagacgt    4320
tgcctgagaa gaagtggctg ccacacccag gggaaggccc tgaggcggag ctgtgctcc     4380
gccatggtgt cccggtacct tccatacaca gaggagtgca gccttctcca tatctcctgg    4440
ccctgtccca ggccggccca gatgtgtccc cccaggcct tgtcctacgt ccaaggtggc     4500
agatgtcttc cctgggctgc caccagcccc cgccccagag tgcccaccg tggcactaga     4560
atgcaagtat cctgcgacct tgcaacctca ccttcctgtg ggtgttcttt cctgccctgt    4620
ccaaaagcgc cctcactatt cttggaccat gccagattct gcctctctgg aaagaggctc    4680
tggacagcag aagcctccaa gcacagagcc tggccccagg ccccagacag ggtgggcttc    4740
ctgcccttcc ctctgggcac gcctgctggc cgacccactg acccactcgg atggaccaac    4800
ctgtctctgtc cccaaaggac gcctgcagga gagagcagca ctccgcatca cctcaccaag   4860
gatcggactc tgcccctgga cctgggaacg actggactgt cacggggttc cctcctagct   4920
ctcccagtga actcctgcca ggcacacaca gcccctatag cactgagctc acatgggact   4980
gggatatggg ggcatctctt ccccagagag gcactcagtg agcctcctgt gcctggcccc   5040
agcctgggcc atctcttagg tgagacagtt gcccgaaact aagccaggcc tggctggagg   5100
agcagcagct tggggagagg gatttccctg cagacctcaa gccatcatgc ggtgggtgct   5160
gccatgacag aggctgcacc cctgggccag cggggctgct cacccacctc ttgtgcaagg   5220
tggcctttgt gctgcgcctg caggcagagc tggagccccc agcagaggca ggctgggacg   5280
gaccagcatc tggaagatgt acatagttat ttttctcttt gtggtttctt gtttggtttg   5340
gtttgctttt gacagcttca tttttatttt gacgtcactt tttggccatg taaactattt    5400
gtggcaattt tatgttttta tttatgaata aagaatgcca tttctcacgc cctcta         5456
```

<210> SEQ ID NO 6
<211> LENGTH: 2947
<212> TYPE: DNA
<213> ORGANISM: Homo sapiens

<400> SEQUENCE: 6

```
cgcctccctt ccccctcccc gcccgacagc ggccgctcgg gccccggctc tcggttataa     60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag ttttcaaaa     480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca cacacaaact ttgtacgaaa    780
aacgtttttc accttagcat tttgtgactt ttgtcgaaag ctgcttttcc agggtttccg    840
```

```
ctgtcaaaca tgtggttata aatttcacca gcgttgtagt acagaagttc cactgatgtg      900
tgttaattat gaccaacttg atttgctgtt tgtctccaag ttctttgaac accacccaaa      960
ccacaggaag aggcgtcctt agcagagact gccctaacat ctggatcatc cccttccgca     1020
cccgcctcgg actctattgg gccccaaatt ctcaccagtc cgtctccttc aaaatccatt     1080
ccaattccac agcccttccg accagcagat gaagatcatc gaaatcaatt tgggcaacga     1140
gaccgatcct catcagctcc caatgtgcat ataaacacaa tagaacctgt caatattgat     1200
gacttgatta gagaccaagg atttcgtggt gatggaggat caaccacagg tttgtctgct     1260
accccccctg cctcattacc tggctcacta actaacgtga aagccttaca gaatctccA     1320 ggacctcagc gagaaaggaa gtcatcttca tcctcagaag acaggaatcg aatgaaaaca     1380
cttggtagac gggactcgag tgatgattgg gagattcctg atgggcagat tacagtggac     1440
aaagaattgg atctggatca tttggaacag tctacaaggg aaagtggcat ggtgatgtgg     1500
cagtgaaaat gttgaatgtg acagcaccta cacctcagca gttacaagcc ttcaaaaatg     1560
aagtaggagt actcaggaaa acacgacatg tgaatatcct actcttcatg ggctattcca     1620
caaagccaca actggctatt gttacccagt ggtgtgaggg ctccagcttg tatcaccatc     1680
tccatatcat tgagaccaaa tttgagatga tcaaacttat agatattgca cgacagactg     1740
cacagggcat ggattactta cacgccaagt caatcatcca cagagacctc aagagtaata     1800
atatatttct tcatgaagac ctcacagtaa aataggtga ttttggtcta gctacagtga     1860
aatctcgatg gagtgggtcc catcagtttg aacagttgtc tggatccatt ttgtggatgg     1920
caccagaagt catcagaatg caagataaaa atccatacag ctttcagtca gatgtatatg     1980
catttggaat tgttctgtat gaattgatga ctggacagtt accttattca aacatcaaca     2040
acagggacca gataattttt atggtgggac gaggatacct gtctccagat ctcagtaagg     2100
tacggagtaa ctgtccaaaa gccatgaaga gattaatggc agagtgcctc aaaaagaaaa     2160
gagatgagag accactcttt ccccaaattc tcgcctctat tgagctgctg gcccgctcat     2220
tgccaaaaat tcaccgcagt gcatcagaac cctccttgaa tcgggctggt ttccaaacag     2280
aggattttag tctatatgct tgtgcttctc caaaaacacc catccaggca gggggatatg     2340
gtgcgtttcc tgtccactga aacaaatgag tgagagagtt caggagagta gcaacaaaag     2400
gaaaataaat gaacatatgt ttgcttatat gttaaattga ataaaatact ctcttttttt     2460
ttaaggtgaa ccaagaaca cttgtgtggt taaagactag atataatttt tccccaaact     2520
aaaatttata cttaacattg gatttttaac atccaagggt taaaatacat agacattgct     2580
aaaaattggc agagcctctt ctagaggctt tactttctgt tccgggtttg tatcattcac     2640
ttggttattt taagtagtaa acttcagttt ctcatgcaac ttttgttgcc agctatcaca     2700
tgtccactag ggactccaga agaagaccct acctatgcct gtgtttgcag gtgagaagtt     2760
ggcagtcggt tagcctgggt tagataaggc aaactgaaca gatctaattt aggaagtcag     2820
tagaatttaa taattctatt attattctta ataatttttc tataactatt tcttttttata     2880 acaatttgga aaatgtggat gtcttttatt tccttgaagc aataaactaa gtttcttttt     2940
ataaaaa                                                                2947
```

<210> SEQ ID NO 7
<211> LENGTH: 6880
<212> TYPE: DNA
<213> ORGANISM: Homo sapiens

<400> SEQUENCE: 7

```
aaaacccttc cctccccgc tccccggaa gtgcttttcc aagattcggg ccggagagag      60
gccttgtagg cacagcggct gagactcgat ctgctccaag taggggctcc agcgcgggtc    120
ggagtctggg ggttcgcgcc cgccgacccg cgccctgctc cctctcagca cctgggcgga    180
cgaaatgacc attaagaagt agatgcccag atgcaaaagt gatgaaacag tccatttgtc    240
ataaagtaag atgcagctgt ggcatgtcaa ccagcttgga acaaaattgt atctgttttt    300
ctcagaagag aattccacaa ggagattttc ttctttctac catcatcaag atcaagcagg    360
caagtttact tgctgtcatc ttctgcaagg ttaaatcagc aaacaaagaa acatggtat     420
tttgaaatat gattaaactc ctgatgctgc agcagaggct aagaatatta atggccagat    480
ctagtgcaca catggtcttc tgaagaagcc atgggtagct gttgtagctg tccagataaa    540
gacactgtcc cagataacca tcggaacaag tttaaggtca ttaatgtgga tgatgatggg    600
aatgagttag gttctggcat aatggaactt acagacacag aactgatttt atacacccgc    660
aaacgtgact cagtaaaatg gcactacctc tgcctgcgac gctatggcta tgactcgaat    720
ctcttttctt ttgaaagtgg tcgaaggtgt caaactggac aaggaatctt tgcctttaag    780
tgtgcccgtg cagaagaatt atttaacatg ttgcaagaga ttatgcaaaa taatagtata    840
aatgtggtgg aagagccagt tgtagaaaga aataatcatc agacagaatt ggaagtccct    900
agaacacctc gaacacctac aactccagga tttgctgctc agaacttacc taatggatat    960
ccccgatatc cctcatttgg agatgcttca tcccatccgt caagcagaca tccttctgtg   1020
ggaagtgctc gcctgccttc agtagggaa gaatctacac atcctttgct tgtggctgag    1080
gaacaagtac atacctatgt caacactaca ggtgtgcaag aagagcggaa aaaccgcaca   1140
agtgtgcatg ttccattgga ggcgagggtt tctaacgctg aaagcagcac accaaaagaa   1200
gaaccaagta gtattgagga cagggatcct cagattcttc ttgaacctga aggagtcaaa   1260
tttgttttag ggccaacccc tgttcaaaag cagttaatgg aaaaagagaa actggagcaa   1320
cttggaagag atcaagttag tggaagtgga gcaaataaca cagaatggga cactggctat   1380
gacagtgatg aacgaagaga tgcaccctct gttaacaaac tggtgtatga aaatataaat   1440
gggctatcta tccctagtgc ctcaggggtc aggagaggtc gtctgacatc caccagtacc   1500
tcagataccc agaatatcaa caactcagct cagagaagaa ctgcattatt aaactatgaa   1560
aatctaccat cttgcctcc tgtttgggaa gcccgcaagc taagtaggga tgaagatgac   1620
aatttaggac caaagacccc atctctaaat ggctaccata taatctaga tccaatgcat   1680
aactatgtaa atacagagaa tgtaacagtg ccagcaagtg ctcacaaaat agaatattca   1740
aggcgtcggg actgtacacc aacagtcttt aactttgata tcagacgccc aagtttagaa   1800
cacaggcagc ttaattacat acaggttgac ttggaaggtg gcagtgactc tgacaaccct   1860
cagactccaa aaacgcctac aactcccctt ccacaaaccc ctaccaggcg cacagagctg   1920
tatgccgtga tagacatcga gagaactgct gctatgtcaa atttgcagaa agcactgcca   1980
cgagatgatg gtacatctag gaaaactaga cacaatagta ctgatctgcc catgtgagcc   2040
tggaaagcat tgtgttgttt gcacctttgt gaagttttta aaaatgaaga tgcaagtgct   2100
tcattttcat ttctaaacac taactccttt tatagactga taaaatttt ttctgaatat    2160
ttcatgtgca tctttaacta aagggaatta atgtagagca ggtactcctt aaagaacact   2220
aatttcatta tatactactc gttgtacagc agcattcccg ttttcacagt gcctatttaa   2280
aatgagagtt gaagtaaatg acatgctggt tgattttat caatattctg gacttaacgc     2340
```

-continued

```
ataccttca tgtctaagtc atggttggct tttaaaactt tttataaagc ctcttgacaa    2400
tgtacattgc taacaggtaa ctataggctt tgaaagtaat gctcgtagat tcagtgttca    2460
cagtatgtgg cctccagcat gtaacatgag gaatccttta tttcattaat taatggcttt    2520
ttgacttgag ccaaaacata tgtaaaggaa acagaagtac cgcacctcct cttacaccag    2580
tcagctcctt tgccttcagt gttactagaa agcggcctgt gtccatgagt gtgctttgct    2640
gttggtgcac tgaaaggcag gaaggagaca agattttcta tttactcatc tcatgatgtc    2700
atttgaaggg catgtccaga tatcttaaaa ttataatagg ctcaagaatc agtctcaggt    2760
cactttaccc aaaaacattt gaaaatctga accacaatct cctgaaagtt tttctcctat    2820
agattgttga caacacattg ttttctggag gcatttgtgc cattaggttt ccatttatct    2880
tcagtttttt tctttggtgt ttgggatgtc ttattttgtt gccttatgtc cttttcaatt    2940
taaaatgttt gagtttgtat atagttttga aattggatta tgtgttcatt gttgtttagt    3000
ttgcattttt gtcaaattat ggttttgaag gttcatttgg aacttactgt tagtctgtaa    3060
cagggttgcc cttgtccagt atttatttat aagctgttta cttttcaagt tgataaaaac    3120
attctccaat tctaaatttg cttgtgtcca taggtgatct ctttagcaaa ctgagaaaaa    3180
aaggaagcta cttttaacat gcaaagttcc ctcaaggtgt accgtgttgt ctctgtgggc    3240
actcttcccc agcactttag cagtaattcc cccagctaca cgctgcagtt gtactctgcc    3300
cactctagtg ttcctcagct ctgctgtcct tttacttgta gctggatctt tgattatcct    3360
tcgatttcca tgaaatatta atattgttgc cagcatagca ggtacagtgg aagtcttgtg    3420
cagtgagatt gtatcataat ttaggattta aaatgaatta agtttatat aaactgaaga    3480 gtctccatat gtcaaactct tggaaaatca aagatgttcc aatttcctaa acactagaga    3540
atacgagaga aggtagagtg gaaaaggtta ggtaaccttg caaaatattt tactattttc    3600
tctaaatatg aggaagtttg agattatgat ctggatctac cagatataac taaggttaat    3660
ttagcatgaa aaagttttag tcatattggc atccaaccta ttcagtaacc gaatcatagg    3720
acaatgatgg attaggagaa caatagagtg ggatcattat aaagaaaata aattattaaa    3780
ggtgtcttta tcgttttagt gccatttta gtgtctttac tataaatcaa tatcagtgta    3840
ttttatcatt ctatgtgcat agcagaattt tcttttctcc cttttgttcc cctgtgaact    3900
tggtgcttat taaagtgctc actgttctct taaaagagag cagtggtata ggtgtgcagt    3960
ttccatgatg caggttccat ttttaatata ttgttccact tatcctttct tctgagtaaa    4020
ttgctaattg tgccaaattt atgtaatagt ttttgtaatg tggaataaga attatgatgg    4080
aaccattgca cattttttc tgaaacagcc agtcaaggca gaacattaat ctccaaatgc    4140
aagggctgat ctatttattc attttggagg ttgggtactt tattctttct ttccgtcatc    4200
cttttcattg tttccccccgg attctaatta gttttatttt ttttagata actccaatat    4260 aatcattaca gttatgctt taaatactat gtgctttaaa aaggaaaatg ggaccaattt    4320
gtctgctaag aatttgattt taggtactat aagagtatta ggaaaatata tacaactggt    4380
gttaatttct agatatttc tagaaatcac ttgtgttcct attttaataaa aggtaattta    4440 gaatactact tgtcctttgc agtagtttag taatgggcat taagctgtgt cctcgaagga    4500
tgtacctatt actaggtgca ttttagaatg aaatattgat attttattag catataattg    4560
tggccatata tctcagattt tctgaggcag atctaattt agataattct gttggtagac    4620
catgtgatcc ttcttttggg ttttggaaat ataatcattg ttaatgtttt ccctccaaat    4680
```

```
agaatactgt tttatccata caaatcataa cagcatctat cccatgctag ggttggaaac    4740
tgatattggt attacttgtg ttttttctta gtgtgtttta tttcccagtt tcatcttctt    4800
ctaaaaatga aaatatggtg ccttccctcc ctccaggaag actggcaaat atttcctttt    4860
atttactgct gctgtggagt gatgagatat gcactttact ctttaagatt cagcaaaaag    4920
cttttcactt ctcagtatat ccagaataca tcatatctgg gacttaggaa aatttgccaa    4980
gcaatctttg tttttataga tactaatgtt gaccctctcc agcgttcaat gttataaata    5040
gaacaagtca agctagtgtt tatctcctcc ccctccccaa aactgtggca cagcatataa    5100
aatgtaccct caataatgttc tattaaaaat gggacagggg ccttatgttt tcataatttc    5160
ccaacaatgt gccgccatat ttttgcctca aggtaaaggt tttaacagat gaaaaagtac    5220
ttcccaattc ccccgtgcta ttcctaacct ataatgccca aatgttttgt gcaatgtgta    5280
gtgtgtgtgt ataaatacat atattcttga aatagacata ccatcagaga catcattcac    5340
aagtaactga tgtattggca tctcattcat atttctgatg tgtgaggtat atggtactaa    5400 ttacctttc cttgatgttt gccaaatttg aataaaggca ttggtacgaa attacagaat    5460
gtaaagaaaa tgttttttggc ttgaaaaatt aacatatttt atgacgtacc acagtatact    5520
ctgcccaaac cagcacccta tctatctttc ctgttcttta catccctgtt ccccatccct    5580
acttcctcat ttttggtata acacagttct tttgtagcat cattataatt gcagttctat    5640
ggcaattgga cagttatagc atggaaacag actggtataa gtagtacagt agtcaccagt    5700
gtgccacatt tgcattagta atgcaaaata tacatttat aaaggacaaa ctttgtgtta    5760
tgttttattt tcattacatt gtataatatt gtaagactat tgtatgtcct aatttgcatt    5820
ataaatgttt ttttcctacg taaaggcata aatatagcaa ctttgtataa aggtagctta    5880
ttagattttt aattttttct tttataaaaa attgtccaac agtgggacta ccattgccaa    5940
attgtatatg aaatatgaat tttaccccca tggttaattt cttttataaa cattccatat    6000
ttctctaata aaaagacata agtgatactg tactatgcat acattgtatc ttaatgctgt    6060
ttcagatcag catttaaat tttggtttgc attttaata ttggcaaaac gtaaccactg    6120
ttaattaaaa taaaaccttg ttgtatatgt aacaacataa ttttccctct atcccttccc    6180 acccttgtt ctctatttct ccctatcagt gccaacttca tacattttgt agcatggcaa    6240
taaaatataa cttttacact gaggccgagt gtggcttttt ggaggaagtg gggatgggac    6300
gattgccctc tagttgtcct tgcatatga ctgttttttg ccatataagc catgtcatca    6360
ggcatgaaaa gttttctcat atatgatgta aacttgcttt taaggacaag tgtgaatgtg    6420 cttttaagc ttaattttg tcatgacaac taatttttt tatctttgga gaagtcagag    6480
ttctttacaa tcaaacgttt attaactgga gtacttagaa taagctagta attgaattta    6540
gttcaagggc taagcaacac atttttaaat ccttatttat tgtagagtat tagtatactg    6600
tcctacaaat tatgtaaaat atggtttaat attagatgac tttggatttt gcaatgcctt    6660
actgttgtca ttctagcata aatatccata atgaggtact caagttgata ctggaagctg    6720
agctgatcat acactgacct gaagcattca tgaaaagctg ctttattgaa taaagtctga    6780
ttggagttct tttcatgctc actttcccct tattgctgaa agtagattgc aataaaaccc    6840
caataaaacg tttggtcgga taaaaaaaaa aaaaaaaaa                          6880
```

<210> SEQ ID NO 8
<211> LENGTH: 346
<212> TYPE: PRT
<213> ORGANISM: Homo sapiens

<400> SEQUENCE: 8

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345
```

<210> SEQ ID NO 9
<211> LENGTH: 347
<212> TYPE: PRT
<213> ORGANISM: Homo sapiens

<400> SEQUENCE: 9

```
Met Ser Ala Leu Gly Ala Val Ile Ala Leu Leu Leu Trp Gly Gln Leu
1               5                   10                  15
```

Phe Ala Val Asp Ser Gly Asn Asp Val Thr Asp Ile Ala Asp Asp Gly
             20                  25                  30

Cys Pro Lys Pro Glu Ile Ala His Gly Tyr Val Glu His Ser Val
         35                  40                  45

Arg Tyr Gln Cys Lys Asn Tyr Tyr Lys Leu Arg Thr Glu Gly Asp Gly
     50                  55                  60

Val Tyr Thr Leu Asn Asn Glu Lys Gln Trp Ile Asn Lys Ala Val Gly
 65                  70                  75                  80

Asp Lys Leu Pro Glu Cys Glu Ala Val Cys Gly Lys Pro Lys Asn Pro
                 85                  90                  95

Ala Asn Pro Val Gln Arg Ile Leu Gly Gly His Leu Ala Lys Gly
             100                 105                 110

Ser Phe Pro Trp Gln Ala Lys Met Val Ser His His Asn Leu Thr Thr
             115                 120                 125

Gly Ala Thr Leu Ile Asn Glu Gln Trp Leu Leu Thr Thr Ala Lys Asn
130                 135                 140

Leu Phe Leu Asn His Ser Glu Asn Ala Thr Ala Lys Asp Ile Ala Pro
145                 150                 155                 160

Thr Leu Thr Leu Tyr Val Gly Lys Lys Gln Leu Val Glu Ile Glu Lys
                 165                 170                 175

Val Val Leu His Pro Asn Tyr Ser Gln Val Asp Ile Gly Leu Ile Lys
             180                 185                 190

Leu Lys Gln Lys Val Ser Val Asn Glu Arg Val Met Pro Ile Cys Leu
         195                 200                 205

Pro Ser Lys Asp Tyr Ala Glu Val Gly Arg Val Gly Tyr Val Ser Gly
     210                 215                 220

Trp Gly Arg Asn Ala Asn Phe Lys Phe Thr Asp His Leu Lys Tyr Val
225                 230                 235                 240

Met Leu Pro Val Ala Asp Gln Asp Gln Cys Ile Arg His Tyr Glu Gly
                 245                 250                 255

Ser Thr Val Pro Glu Lys Lys Thr Pro Lys Ser Pro Val Gly Val Gln
             260                 265                 270

Pro Ile Leu Asn Glu His Thr Phe Cys Ala Gly Met Ser Lys Tyr Gln
         275                 280                 285

Glu Asp Thr Cys Tyr Gly Asp Ala Gly Ser Ala Phe Ala Val His Asp
     290                 295                 300

Leu Glu Glu Asp Thr Trp Tyr Ala Thr Gly Ile Leu Ser Phe Asp Lys
305                 310                 315                 320

Ser Cys Ala Val Ala Glu Tyr Gly Val Tyr Val Lys Val Thr Ser Ile
                 325                 330                 335

Gln Asp Trp Val Gln Lys Thr Ile Ala Glu Asn
             340                 345

<210> SEQ ID NO 10
<211> LENGTH: 117
<212> TYPE: PRT
<213> ORGANISM: Homo sapiens

<400> SEQUENCE: 10

Gln Asp Asn Thr Arg Lys Ile Ile Ile Lys Asn Phe Asp Ile Pro Lys
1               5                   10                  15

Ser Val Arg Pro Asn Asp Glu Val Thr Ala Val Leu Ala Val Gln Thr
             20                  25                  30

Glu Leu Lys Glu Cys Met Val Val Lys Thr Tyr Leu Ile Ser Ser Ile

```
                35                   40                  45
Pro Leu Gln Gly Ala Phe Asn Tyr Lys Tyr Thr Cys Leu Cys Asp Asp
        50                  55                  60

Asn Pro Lys Thr Phe Tyr Trp Asp Phe Tyr Thr Asn Arg Thr Val Gln
65                  70                  75                  80

Ile Ala Ala Val Val Asp Val Ile Arg Glu Leu Gly Ile Cys Pro Asp
                85                  90                  95

Asp Ala Ala Val Ile Pro Ile Lys Asn Asn Arg Phe Tyr Thr Ile Glu
               100                 105                 110

Ile Leu Lys Val Glu
        115

<210> SEQ ID NO 11
<211> LENGTH: 93
<212> TYPE: PRT
<213> ORGANISM: Homo sapiens

<400> SEQUENCE: 11

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```